United States Patent [19]

Emmons et al.

[11] 4,155,892

[45] May 22, 1979

[54] POLYURETHANE THICKENERS FOR AQUEOUS COMPOSITIONS

[75] Inventors: William D. Emmons, Huntingdon Valley; Travis E. Stevens, Ambler, both of Pa.

[73] Assignee: Rohm and Haas Company, Philadelphia, Pa.

[21] Appl. No.: 838,690

[22] Filed: Oct. 3, 1977

Related U.S. Application Data

[60] Division of Ser. No. 686,751, May 17, 1976, Pat. No. 4,079,028, which is a continuation-in-part of Ser. No. 619,549, Oct. 3, 1975, abandoned.

[51] Int. Cl.$^2$ ............................................. C08G 18/00
[52] U.S. Cl. ................... 260/29.2 TN; 8/1 R;
8/76; 8/79; 71/69; 260/29.6 NR; 260/29.7 NR; 424/358; 428/425
[58] Field of Search ............... 260/29.2 TN, 29.6 NR, 260/29.7 NR; 8/79, 76, 1 R; 428/425; 424/358; 71/69

[56] References Cited

U.S. PATENT DOCUMENTS

| | | | |
|---|---|---|---|
| 2,946,767 | 7/1960 | Gassmann | 260/29.6 NR |
| 2,948,691 | 8/1960 | Windemuth et al. | 260/2.5 BB |
| 3,086,887 | 4/1963 | Habib | 260/9 |
| 3,189,578 | 6/1965 | Kuemmerer | 260/29.2 TN |
| 3,190,847 | 6/1965 | Mitchell et al. | 260/29.6 NR |
| 3,360,494 | 12/1967 | Bolinger | 260/29.6 NR |
| 3,490,987 | 1/1970 | Bauriedel | 260/77.5 AM |
| 3,708,435 | 1/1973 | Starkman | 260/29.2 TN |
| 3,770,684 | 11/1973 | Singer et al. | 260/29.7 NR |
| 3,923,713 | 12/1975 | Hermann | 260/29.2 TN |
| 3,988,278 | 10/1976 | Bartizal | 260/29.2 TN |
| 3,996,154 | 12/1976 | Johnson et al. | 260/29.2 TN |

FOREIGN PATENT DOCUMENTS

2054885 5/1972 Fed. Rep. of Germany ... 260/29.6 NR

*Primary Examiner*—Maurice J. Welsh
*Attorney, Agent, or Firm*—Patrick C. Baker

[57] ABSTRACT

Latex and other aqueous systems are thickened by incorporation of a low molecular weight polyurethane characterized by at least three hydrophobic groups interconnected by hydrophilic polyether groups. The thickeners are nonionic, hydrolytically stable and are resistant to biodegradation.

19 Claims, No Drawings

POLYURETHANE THICKENERS FOR AQUEOUS COMPOSITIONS

RELATED APPLICATION

This is a division of application Ser. No. 686,751 filed May 17, 1976, which is a continuation-in-part application of Ser. No. 619,549, filed Oct. 3, 1975, now abandoned. Ser. No. 686,751 is now U.S. Pat. No. 4,079,028 issued Mar. 14, 1978.

BACKGROUND OF THE INVENTION

This application relates to a new class of nonionic polyurethanes useful for thickening a wide range of aqueous systems, and more particularly relates to relatively low molecular weight thickeners, characterized by hydrolytic stability, versatility and efficiency, and to a wide vareity of aqueous systems containing the thickeners.

Since ancient times additives have been sought for aqueous systems to increase the viscosity and to maintain the viscosity at required levels under specified processing conditions and end use situations. For this reason such additives are commonly called "thickeners", although the additives often impart or improve other properties as well in a particular system. For example, thickeners are used in latex paints not only for viscosity improvement and control, but also for protective colloidal action and for improvement of pigment suspension, leveling and flow. In addition, the additives often emulsify, disperse and stabilize latex ingredients and are themselves film formers. Such additives, especially in latex paint and textile treating compositions, improve the "sticking" or binding properties of the composition. In water-based coloring compositions, such as pigment printing pastes and acid dye baths, thickeners are utilized for their suspending properties. In textile treating compositions, thickeners are sought which also improve softening, sizing and handling properties. Thickeners are commonly used in cosmetics for thixotropy and to improve body, smoothness and silkiness. As additives to paper coating compositions, thickeners improve thickening under high shear conditions. Thickeners are likewise useful for the foregoing and other properties in oil well drilling and flooding fluids, fire-fighting foams and fluids, detergents, leather pastes and finishes, adhesives, pharmaceuticals, agricultural formulations, and emulsions of all kinds. The list of applications and auxiliary properties of thickeners is virtually endless.

Among the many well-known thickeners may be mentioned natural products such as the alginates, casein, gum karaya, locust bean gum and gum tragacanth, and modified natural products such as the cellulosics, including methyl cellulose, hydroxethyl cellulose and hydroxypropylmethyl cellulose. Totally synthetic thickeners are also available, such as carboxy vinyl ether copolymers, acrylic polymers and maleic anhydridestyrene copolymers. However, all of the known thickeners have deficiencies.

For example, most latex paints are neutral or mildly alkaline and contain various electrolytes. Ionic thickeners are undesirable in such paints because the rheology they impart to the paints is unduly sensitive to pH and to the other ionic ingredients. Ionic thickeners normally are not used at all in paint latices containing polyvalent cations because the latex thereby becomes unstable and any improvement in viscosity achieved by their use will rapidly be lost. Moreover, dried films of latex paints containing ionic thickeners are sensitive to water and to alkaline solutions, and tend to adhere poorly to alkaline substrates such as concrete and mortar. Other thickeners are water and alcohol sensitive, impart poor rheology (such as spatter or ropiness) or are inefficient, requiring unduly high concentrations for effective viscosity improvement and control. Still other thickeners cannot be used in textile treating compositions because of a tendency to impart an undue harshness to the textile. The natural or modified natural thickeners are easily contaminated by various microbial species or are enzymatically degraded and systems containing them therefore require antimicrobial agents or other controls.

The thickeners of the invention exhibit significant improvements over the foregoing and other known thickeners, such as the thickeners disclosed in U.S. Pat. No. 3,770,684 to Singer et al. and in German Pat. No. 2,054,885 assigned to BASF. It could not have been predicted from these patents, for example, that relatively minor amounts (about 1%) of the polymers of this invention would increase the viscosity of water to 1000 cps or more. More importantly, the thickeners of the invention are exceptionally versatile in their ability to impart the special rheological control required in diverse types of thickened systems. Such control is achieved by selecting thickeners and blending them with various aqueous systems in fashions not taught by the prior art.

The thickeners of this invention provide a combination of properties not found in any one class of known thickeners. For example, they are nonionic and in many cases are highly efficient viscosity improvers although having a relatively low molecular weight. They are stable to water and alcohol and are not sensitive to biodegradation. They are versatile in that not only do they thicken virtually unlimited types of aqueous systems, but they also impart many of the auxiliary properties described above. Thus, as additives to textile binder compositions, they actually soften rather than harden the fabric. In latex paints, especially, they not only thicken but in many cases also provide superior flow and leveling, and give excellent viscosity control under both low and high shear conditions.

SUMMARY

The thickeners of the invention are urethane polymers having at least three low molecular weight hydrophobic groups at least two of which are terminal (external) hydrophobic groups. Many of the polymers also contain one or more internal hydrophobic groups. The hydrophobic groups together contain a total of at least 20 carbon atoms and are linked through hydrophilic (water soluble) groups containing polyether segments of at least about 1500, preferably at least about 3000, molecular weight each so that the polymers readily solubilize in water, either by self-solubilization or through interaction with a known solubilizing agent such as a water miscible alcohol or surfactant. The molecular weight of the polyurethanes is of the order of about 10,000 to 200,000.

The polymers are prepared in non-aqueous media and are the reaction products of at least reactants (a) and (c) of the following reactants: (a) at least one water soluble polyether polyol, (b) at least one water insoluble organic polyisocyanate, (c) at least one monofunctional hydrophobic organic compound selected from monofunctional active hydrogen compounds and organic monoisocyanates, and (d) at least one polyhydric alcohol or polyhydric alcohol ether. The products formed include the following:

(1) Reaction products of a reactant (a) containing at least three hydroxyl groups, and the foregoing organic monoisocyanates;

(2) Reaction products of reactant (a), reactant (b) containing two isocyanate groups, and the foregoing active hydrogen containing compounds. Such compounds wherein the ratio of equivalents of (a) to (b) is 0.5:1 to 1:1 are believed to be new per se; all are believed to be useful in certain systems;

(3) Reaction products of reactant (a), reactant (b) containing at least three isocyanate groups, and the active hydrogen containing compounds;

(4) Reaction products of reactant (a), reactant (b) and the organic monoisocyanates; and (5) Reaction products of reactants (a), (b), (d) and the organic monoisocyanates.

The reactants are normally employed in substantially stoichiometric proportions, that is, the ratio of total equivalents of active hydrogen containing reactants (whether mono or polyfunctional) to isocyanate reactants is at least 1:1. A slight stoichiometric excess (e.g., about 5–10%) of monofunctional active hydrogen containing compound may be used to eliminate any unreacted isocyanate functionality, thus avoiding toxicity from this source. Greater excesses, particularly of capping hydroxyl compound, may be used to increase thickening efficiency. A slight excess of a monoisocyanate is sometimes desirable in cases where such isocyanate is a capping hydrophobe, to ensure capping of all available active hydrogen functionality.

By "monofunctional active hydrogen compound" is meant an organic compound having only one group which is reactive with isocyanate, such group therefore containing an active hydrogen atom, any other functional groups, if present, being substantially unreactive to isocyanate. Such compounds include monohydroxy compounds such as alcohols, alcohol ethers and monoamines, as well as polyfunctional compounds providing the compound is only monofunctional to isocyanates. For example, the primary amines, although difunctional in many reactions, are only monofunctional towards isocyanates, the hydrogen atom in the resulting urea group being relatively unreactive to isocyanate as compared with the hydrogen atom of the amino group or of unhindered alcohols.

Reactant (c) is a "capping" compound, meaning it reacts with ("caps") the terminal functional groups of the reaction product of reactants (a) and (b).

The polyether polyol reactant (a) is an adduct of an alkylene oxide and a polyhydric alcohol or polyhydric alcohol ether, a hydroxyl-terminated prepolymer of such adduct and an organic polyisocyanate, or a mixture of such adducts with such prepolymers.

Reactant (d) may be employed to terminate isocyanate functionality or to link isocyanate-terminated reaction intermediates. Reactant (d) may be a polyhydric alcohol or polyhydric alcohol ether of the same type as used to form the adducts of reactant (a). The polyhydric alcohols or alcohol ethers may be aliphatic, cycloaliphatic or aromatic and may be used singly or in mixtures of either type or mixtures of the two types.

The organic polyisocyanates include simple di- and triisocyanates, isocyanate-terminated adducts of such polyhydric alcohols and organic di- or triisocyanates, as well as isocyanate-terminated prepolymers of polyalkylene ether glycols and organic di- or triisocyanates.

The hydrophobic groups of the polyurethanes occur in the residues of reactants (b) and (c) and may also occur in the residue of reactant (d) if present. The terminal (external) hydrophobes are the residues of the monofunctional active hydrogen compounds, organic monoisocyanates, or combinations of the residues of such compounds.

By appropriate selection of reactants and reaction conditions, including proportions and molecular weights of reactants, a variety of polymeric products may be obtained. The products exhibit good thickening properties due to the presence and distribution therein of hydrophilic (polyether) groups (residues of the polyol reactant) and hydrophobic groups (residues of hydroxy compounds, amines and/or isocyanates). From a structural standpoint the products may be classified into three groups as described hereinbelow. Some of the polymers have readily identifiable structures, such as the essentially linear structures of formulas I–IV and the generally star-shaped structures of formulas V–VII. The remaining polymers are complex mixtures.

The polymers may be substituted for known thickeners in any aqueous system in which thickeners are normally utilized and therefore the fields of use of the thickeners of the invention include a host of industrial, household, medical, personal care and agricultural compositions. As indicated above, thickening in such compositions is often also accompanied by other improvements, such as leveling, flow, stabilization, suspension, high and low shear viscosity control, and binding properties. While all of the polymers of Groups A, B and C are useful as thickeners for latex paints and many other aqueous systems, preferred thickeners for pigment printing pastes and acid dye baths are those of Groups B and C.

In this specification the term "hydrophobe" includes not only the hydrocarbon residues of hydroxyl, amino or isocyanate reactants but also the combination of such residues with next adjacent urethane and other groups remaining in the structure after reaction. The term "hydrophobe" or like term therefore is used herein to mean all those portions or segments of the polymeric reaction products which contribute to water insolubility. All portions or segments other than the residues of the polyether polyol reactants therefore are hydrophobic.

DESCRIPTION OF THE POLYMERS

The polymeric thickeners useful according to the invention are polyurethanes which may be classified as follows:

Group A—Linear Products

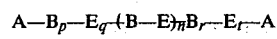

where each of p, q, r and t independently is zero or 1; at least one of q and r is 1, and t is zero when r is zero; provided that, when q is 1, then (a) each of p, r and t is zero (as in formula I, below); or (b) p is zero and each of r and t is 1 (as in formula II, below); or (c) t is zero and each of r and p is 1 (as in formula III, below); and when q is zero, then r is 1 and each of p and t is zero (as in formula IV, below).

Polymers coming within the foregoing formula are:

|   | Examples |
|---|---|
| I. A—E—(B—E)—$_n$A | 1–17A |
| II. A—E—(B—E)$_n$—B—E—A | 75–96B |
| III. A—B—E—(B—E)$_n$—B—A | 97–102 |
| IV. A—(B—E)$_n$—B—A | 18–74T |

The equivalent ratio of total active hydrogen to total isocyanate in the Group A compounds is about 1:1 to 2:1.

Group B—Star-Shaped Products

[H—E—OCH$_2$]$_s$L[Q$_v$—(D$_u$—E—A)$_w$R$_z$]$_m$ where L is X, Y or —O—, Q is —CH$_2$C≡, D is —CH$_2$O—, m is 2–4, s is zero to 2, the sum of m and s is the valence of L (2–4), w is 1–3, and each of u and z independently is zero or 1;
and where X is a hydrocarbon radical containing at least 1 carbon atom, preferably 1–4 carbon atoms; and Y is a trivalent radical selected from
—OCONH(CH$_2$)$_6$N[CONH(CH$_2$)$_6$NHCO—O]$_2$, CH$_3$C[CH$_2$O—OCNHC$_7$H$_6$NHCO]$_3$ and CH$_3$CH$_2$C[CH$_2$O—OCNHC$_7$H$_6$NHCO]$_3$;
provided that,
(a) when L is X, then u and w are each 1, v and z are each zero, the sum of m and s is 4, and m is at least 2 (as in formula V below);
(b) when L is Y, then u, v and s are each zero, m is 3, w is 2–3, and z is zero or 1 (as in formula VI below); and
(c) when L is —O—, then v and u are each 1, w is 1–3, m is 2 and each of s and z is zero (as in formula VII below);
Polymers coming within the foregoing formula are:

|   | Examples |
|---|---|
| V. (H—E—OCH$_2$)$_s$X[CH$_2$O—E—A]$_m$ | 103–115 |
| VI. Y[(E—A)$_w$R]$_3$ | 116–140 |
| VII. O[CH$_2$O{CH$_2$O—E—A}$_3$]$_2$ | 141–153 |

In each of the polymers of Groups A and B:
A and R are hydrophobic organic radicals containing at least one carbon atom;
B is a divalent hydrophobic group of the structure $$-\overset{O}{\underset{\|}{C}}NH-G-NH\overset{O}{\underset{\|}{C}}-O-$$

where G is the residue of an organic di- or triisocyanate, the residue having no remaining unreacted isocyanate groups;
E is a divalent, hydrophilic, nonionic polyether group; and
n is at least 1, such as about 1–20, preferably 1–10.

In structures V and VII the equivalent ratio of total active hydrogen to total isocyanate is from about 1.2:1 to a stoichiometric excess of isocyanate; and in structure VI from about 1:1 to a stoichiometric excess of active hydrogen.

It will be apparent to the polymer chemist that values of n given in this specification are average rather than absolute values since in reaction products of the type of this invention, the reaction product will often be a mixture of several products having different values for n.

The star-shaped polymer configurations of formulas V–VII result from a polyhydric reactant such as trimethylolpropane or pentaerythritol (residue X in formula V) or a triisocyanate (residue Y in formula VI), or result from a polyhydroxy ether such as dipentaerythritol (Q and D of formula VII). L, Q and D form a central hydrophobic nucleus from which radiate hydrophilic polyether segments E, partially or fully capped (terminated) with hydrophobic groups A and R. The points or arms may have the same or different chain length and may contain hydrophobic segments alternating with hydrophilic portions. When s is greater than zero, partial capping results. In formulas V and VII, A is the residue of an organic monoisocyanate.

Group C—Complex Polymers

The polymers of Group C are complex mixtures of linear, branched and sub-branched products which form networks of hydrophobes and hydrophobic segments interspersed with hydrophilic segments. The products result from the multitude of different interactions which may take place between the polyfunctional reactants used to form them. The essential reactants are a polyfunctional compound containing at least three hydroxyl or isocyanate groups, a difunctional compound reactive with the polyfunctional compound, and a monofunctional reactant such as a monohydroxy or monoamino compound. The reactants may each be present singly or in mixtures of two or more. The difunctional compound is a diisocyanate (for reaction with the triol or higher polyol) or a diol (for reaction with the triisocyanate) and can also be present singly or in mixtures of two or more. The monohydroxy or monoamino compound, or mixture thereof, is added to the reaction mixture to cap isocyanate of the triisocyanate not reacted with the diol in order to prevent gelation. A monoisocyanate may be added to the reaction mixture if some of the polyol (diol, triol or higher polyol) remains unreacted or if it is desired to cap all hydroxyl groups.

It should be understood that in preparing the products of Group C as well as those of Groups A and B, capping of all hydroxyl is not required. Capping or hydrolyzing of all isocyanate, although not absolutely necessary, is preferred to avoid toxicity in the polymeric product. Generally, no more than about 25% of the hydroxyl should remain uncapped since the hydroxyl increases the water solubility and reduces thickening efficiency. Of course, if the product contains a relatively high proportion of hydrophobic residues, a greater amount of uncapped hydroxyl can be tolerated.

In summary, the Group C products are polymeric compositions prepared by reacting: (a) a polyfunctional reactant selected from an organic polyol having at least three hydroxyl groups, an organic polyisocyanate having at least three isocyanate groups, and mixtures thereof; (b) a difunctional reactant selected from an organic diol, an organic diisocyanate, and mixtures thereof, the diol being present in the reaction mixture when the polyisocyanate is present and the diisocyanate being present when the polyol is present; (c) a monofunctional hydroxyl or amino compound in an amount sufficient to cap any unreacted isocyanate remaining from the reaction of reactants (a) and (b) and to prevent gelation of the reaction mixture; and optionally (d) a hydrophobic organic monoisocyanate to cap hydroxyl groups remaining from the reaction of reactants (a) and (b); wherein at least one of the polyol and diol contains at least one water soluble polyether segment of at least 1500 molecular weight, wherein the total carbon content of all hydrophobic groups is at least 20 and the average molecular weight of the polyurethane product is about 10,000-200,000. Examples 154-225 below illustrate these products.

As a general rule, the foregoing conditions are true for all of the polymers of Groups A, B and C. That is, the polymers will provide good thickening if the polyether segments have molecular weights of at least 1500 (preferably 3,000-20,000), the polymers contain, on the average, at least three hydrophobic groups and at least two water soluble polyether segments linking the hydrophobes, the sum of the carbon atoms in the hydrophobic groups being at least 20, preferably at least 30, and the total molecular weight is about 10,000-200,000, preferably 12,000-150,000. The optimum polyether content will depend, of course, on the bulk and distribution of the hydrophobic groups in the polymer. Whereas a total polyether molecular weight of 4,000-5,000 may be suitable when the polymer contains small external and internal hydrophobes, the polyether content may have to be substantially increased when heavier and/or more extensively branched hydrophobic groups are to be built into the polymer, such as long chain fatty polyols or amines. About 200 carbon atoms in the hydrophobic portion is the practical upper limit although it will be understood that it is a relative matter since the proportion of polyether may be increased to offset increased hydrophobicity. However, as total molecular weight increases the viscosity increases and ease of handling decreases, and therefore the economic usefulness of the products is substantially diminshed.

The relatively low molecular weights of the polymers in conjunction with their nonionic character promote their efficiency as thickeners, since their thickening capabilities are much greater for equivalent molecular weight in a given aqueous system, as compared with known thickeners, and the polymers are believed to thicken by an associative mechanism such as micellar or other form of association, rather than by molecular weight or chain extension alone. For example, 1.0% by weight of the polymers in an aqueous dispersion will provide thickening equivalent to that afforded by other nonionic thickeners at much higher concentrations. Of course, the ability to obtain good thickening at relatively low molecular weight and solids levels also promotes other properties, such as softening effects on fabrics when the polymers are used in fabric finishing compositions. In addition, the use of organic isocyanate residues as internal or external hydrophobes also makes the polymers relatively stable to hydrolytic degradation, thereby greatly expanding their usefulness, as in systems requiring extended shelf life.

In certain applications, such as latex paints, polymers of the invention can provide excellent flow and leveling as well as thickening. In other applications, such as paper coating compositions where high shear thickening is important, polymers of the invention can easily be selected which are superior in this respect, while also retaining good thickening capabilities and low shear viscosity.

PREPARATION OF THE POLYMERIC PRODUCTS

The first class of reactants (a) used to form the polyurethanes of the invention are water soluble polyether polyols. Typically, these are adducts of an aliphatic, cycloaliphatic or aromatic polyhydroxy compound such as a polyhydric alcohol or polyhydric alcohol ether and an alkylene oxide such as ethylene oxide or propylene oxide, or they may be hydroxyl-terminated prepolymers of such adducts and an organic polyisocyanate. The adducts or prepolymers may be mixtures of two or more of such adducts or prepolymers, and mixtures of such adducts with prepolymers may also be used. The polyhydric alcohols include not only the simple glycols such as ethylene glycol and propylene glycol but also hydroxy compounds containing three or more hydroxyl groups, such as polyalkylolalkanes (e.g., trimethylol propane, pentaerythritol) and polyhydroxyalkanes (e.g., glycerol, erythritol, sorbitol, mannitol, and the like). The polyhydric alcohol ethers usually are adducts of polyhydric alcohols and alkylene oxides but in some cases are present as byproducts with other polyhydroxy compounds. For example, pentaerythritol as ordinarily prepared contains about 15% of the ether, dipentaerythritol. Typical of cycloaliphatic polyhydric compounds are cyclopentandiol-1,2,1,4-cyclohexandiol, hexahydroxycyclohexane, and the like. The polyhydroxy compounds also include aromatic compounds such as di- and trihydroxy benzene and the like.

The foregoing and numerous other hydroxyl compounds, adducts and prepolymers are well known and thoroughly described in the technical literature, including standard textbooks such as Whitmore, *Organic Chemistry*, 2d Ed., Dover Publications, Inc., New York, 1961, two volumes, pages 302-330, 547-559 and 671-674.

A convenient source of the hydrophilic polyether polyol adducts is a polyalkylene glycol (also known as a polyoxyalkylene diol) such as polyethylene glycol, polypropylene glycol or polybutylene glycol, of about 4,000-20,000 molecular weight. However, adducts of an alkylene oxide and a monofunctional reactant such as a fatty alcohol, a phenol or an amine, or adducts of an alkylene oxide and a difunctional reactant such as an alkenolamine (e.g., ethanolamine) are also useful. Such adducts are also known as diol ethers and alkanolamine ethers.

Suitable compounds providing polyether segments also include amino-terminated polyoxyethylenes of the formula $NH_2(CH_2CH_2O)_xH$ where x ranges from about 10 to 200. Such compounds are sold under the trademark "Jeffamine", a typical compound being "Jeffamine 2000" of about 2000 molecular weight.

The second class of reactants (b), the water insoluble organic polyisocyanates, or isocyanates used to form the hydroxyl-terminated prepolymers included among reactants (a), may be aliphatic, cycloaliphatic or aromatic, such as the following, and may be used singly or in admixture of two or more thereof including mixtures of isomers:

1,4-tetramethylene diisocyanate
1,6-hexamethylene diisocyanate ("HDI")
2,2,4-trimethyl-1,6-diisocyanatohexane
1,10-decamethylene diisocyanate
1,4-cyclohexylene diisocyanate
4,4'-methylenebis(isocyanatocyclohexane)
1-isocyanato-3-isocyanatomethyl-3,5,5-trimethylcyclohexane
m- and p-phenylene diisocyanate
2,6- and 2,4-tolylene diisocyanate ("TDI")
xylene diisocyanate
4-chloro-1,3-phenylene diisocyanate
4,4'-biphenylene diisocyanate
4,4'-methylene diphenylisocyanate ("MDI")
1,5-naphthylene diisocyanate
1,5-tetrahydronaphthylene diisocyanate polymethylene polyphenylisocyanates sold under the brand name "PAPI," such as "PAPI 135" (equivalent weight of 133.5 and average isocyanate functionality of 2.7) and "PAPI 901" (equivalent weight of 133 and average isocyanate functionality of 2.3)

aromatic triisocyanate adduct of trimethylol propane and tolylene diisocyanate sold under the brand name "Mondur CB-75".

aliphatic triisocyanate product of the hydrolytic trimerization of 1,6-hexamethylene diisocyanate, sold under the brand name "Desmodur N"

$C_{36}$dimer acid diisocyanate sold under the brand name "DDI", based on dimer acids as discussed in J. Am. Oil Chem. Soc. 51, 522 (1974)

The monoisocyanates representative of one form of reactant (c) include straight chain, branched chain and cyclic isocyanates such as butyl isocyanate, octyl isocyanate, dodecyl isocyanate, octadecyl isocyanate, cyclohexyl isocyanate and the like. These isocyanates also may be used singly or in mixtures of two or more thereof and are a convenient method of introducing terminal hydrophobes into the polymer.

The mono or polyisocyanates also include any polyfunctional isocyanate derived from reaction of any of the foregoing isocyanates and an active hydrogen compound having a functionality of at least two, such that at least one isocyanate group remains unreacted. Such isocyanates are equivalent to chain-extending an isocyanate terminated isocyanate/diol reaction product with a reactant containing at least two active hydrogen atoms in a manner well known in polyurethane synthesis.

A variety of other useful mono- or polyisocyanates are set forth in texts on urethane chemistry, including "Advances In Urethane Science and Technology", K. S. Frisch and S. L. Reegan, editors, Technomic Publishing Co., Inc., Volume 1 (1971) and Volume 2 (1973), and references cited therein. The isocyanates may contain any number of carbon atoms effective to provide the required degree of hydrophobic character. Generally, about 4 to 30 carbon atoms are sufficient, the selection depending on the proportion of the other hydrophobic groups and hydrophilic polyether in the product.

Representative of monofunctional active hydrogen compounds of the third class of reactants (c) wherein the functional group is hydroxyl are the fatty ($C_1$-$C_{24}$) alcohols such as methanol, ethanol, octanol, dodecanol, tetradecanol, hexadecanol, and cyclohexanol; phenolics such as phenol, cresol, octylphenol, nonyl and dodecyl phenol; alcohols ehters such as the monomethyl, monoethyl and monobutyl ethers of ethylene glycol, and the analogous ethers of diethylene glycol; alkyl and alkaryl polyether alcohols such as straight or branched ($C_1$-$C_{22}$) alkanol/ethylene oxide and alkyl phenol-/ethylene oxide adducts (e.g., lauryl alcohol, t-octylphenol or nonylphenolethylene oxide adducts containing 1-250 ethylene oxide groups); and other alkyl, aryl and alkaryl hydroxy compounds including mixtures thereof, such as $C_{10}$-$C_{20}$ normal alcohol mixtures known as "Alfol" alcohols.

Amino compounds, which may be used in place of all or a portion of the monohydroxy compounds as monofunctional active hydrogen compounds, are primary or secondary aliphatic, cycloaliphatic or aromatic amines such as the straight or branched chain alkyl amines, or mixtures thereof, containing about 1-20 carbon atoms in the alkyl group. Suitable amines include n- and t-octyl amine, n-dodecyl amines, $C_{12}$-$C_{14}$ or $C_{18}$-$C_{20}$ t-alkyl amine mixtures, and secondary amines such as N,N-dibenzyl amine. N,N-dicyclohexyl amine and N,N diphenyl amine. The lower alkyl ($C_1$-$C_7$) amines may be used if there is sufficient hydrophobic residue in the product from other sources such as isocyanate or hydroxyl compound to provide a total of at least ten carbon atoms in the terminal groups (taken together) of the polymeric products. The amino compounds may contain more than one active hydrogen atom provided that under normal reaction conditions it is only monofunctional towards an isocyanate group. A primary amine is an example of such a compound.

The foregoing and numerous other useful monohydroxy and amino compounds are well known as described in standard organic textbooks and other reference works, such as the Whitmore text noted above, as on pages 102-138 and 165-170.

The polymers are prepared according to techniques generally known for the synthesis of urethanes preferably such that no isocyanate remains unreacted. Water should be excluded from the reaction since it will consume isocyanate functionality. Anhydrous conditions are accomplished by azeotropic distillation to remove water, by heating under a nitrogen sparge, or by prior drying of reactants.

If desired, the reaction may be run in a solvent medium in order to reduce viscosity in those reactions leading to higher molecular weight products. High viscosity in the reaction medium causes poor heat transfer and difficult mixing. Generally, a solvent is useful when molecular weights of 30,000 or higher are encountered. Below this molecular weight a solvent is not required. When used, the solvent should be inert to isocyanate and capable of dissolving the polyoxyalkylene reactant and the urethane product at reaction temperature. Suitable inert solvents include non-active hydrogen containing compounds such as benzene, toluene, xylene and other well-known solvents rich in aromatic hydrocarbons such as the solvents sold under the trademarks "Solvesso 100" or "Solvesso 150", as well as esters such as ethyl acetate, butyl acetate and "Cellosolve" acetate, and dialkyl ethers of ethylene glycol, diethylene glycol, and the like. Many other well-known solvents can also be used.

Reaction temperature is not critical. A convenient reaction temperature is about 40° C. to 120° C., preferably about 60° C. to 110° C. Reaction temperature should be selected to obtain reasonably fast reaction rate while avoiding undesirable side reactions, such as isocyanate-urethane condensation.

The order of reactant charging is not critical in most cases. However, in some instances, as where the reactants are higher molecular weight or polyfunctional, order of addition obviously should be controlled to avoid gelation. For example, to avoid high molecular weight while obtaining a good proportion of hydrophobic character, it may be desirable to first charge the hydrophobe-contributing reactant, such as monohydroxy compound, amine or monoisocyanate, followed by the polyoxyalkylene glycol. If higher molecular weight is desired, the hydrophobe-contributing reactant may be charged after the polyoxyalkylene glycol, or a portion of the hydrophobic reactant may be charged initially and the balance added after the remaining reactants. Charging also may be continuous or semi-continuous, if desired.

Order of addition, reactant proportions and other conditions of reaction thus may be varied to control the geometry, molecular weight and other characteristics of the products, in accordance with well-known principles of polyurethane synthesis.

As is evident from their formulas and the Examples following, the Group A polymers are conveniently prepared by forming a prepolymer of a polyoxyalkylene glycol and a diisocyanate, and then capping the prepolymer with a monoisocyanate or mono-diisocyanate mix, when the prepolymer has hydroxyl terminal groups, or with a monohydric or amino compound (or alkylene oxide adduct of a monohydric compound or of an amino compound) when the prepolymer has isocyanate terminal groups.

The Group B polymers are prepared in a similar manner except for use of a polyfunctional compound such as trimethylolpropane or a triisocyanate as a reactant. For example, generally star-shaped polymers result when a trimethylolpropane-ethylene oxide adduct or a triisocyanate is reacted with a monoisocyanate or monohydroxy compound-ethylene oxide adduct, respectively. Suitable polyisocyanates are "Desmodur N" and "Mondur CB-75", described below.

The more complex polymer mixtures of Group C result from reaction of a polyol (at least three hydroxyl groups) or triisocyanate with a diisocyanate or polyether diol, respectively, followed by capping of unreacted isocyanate with a monol or monoamine or capping of unreacted hydroxyl with a monoisocyanate. Examples of suitable polyols are polyalkylolalkanes such as trimethylolpropane or trimethylolbutane, hydroxy compounds having ether linkages such as the erythritols, (dipentaerythritol, tripentaerythritol, and the like) and hydroxyalkanes containing three or more hydroxy groups, such as glycerol, butane tetraol, sorbitol, mannitol, and the like. As indicated, not all of the hydroxyl groups must be capped with monoisocyanate hydrophobes.

Reactant ratios can play an important role in determining the properties of the polymers. For example, when the linear polymers of Group A are prepared from isocyanate-terminated polyethylene glycol (PEG-molecular weight 6000–7500) prepolymers capped with decyl or dodecyl alcohol and where the isocyanate is tolylene diisocyanate (TDI), an alcohol/PEG/TDI equivalent ratio of 0.2–0.3/0.8–0.7/1.0 gives polymers which are excellent thickeners for latex paints. When, however, the ratio is about 0.1/0.9/1.0 the thickening ability is somewhat less but flow and leveling capabilities in the paints are very good. Further description of these and other properties is given below, following disclosure of preparation of the polymers.

Prepolymers, adducts or other reactants containing ester groups should be avoided, due to hydrolytic instability of products containing such groups. However, the reactants may contain any other groups provided such groups are inert, i.e., they do not interfere in formation of the desired products. For example, halogens such as chlorine and bromine normally would not prevent formation of useful polymers.

PRODUCT CONSISTENCY

The consistency of the polymeric thickener products can be controlled either by a solvent reaction medium (mentioned above) or by combining the product with a softening agent after synthesis. Without such treatment the higher molecular weight products tend to be tough and intractible. Depending on the molecular weight of the product, the solids content, and the type and amount of additive, the product can be made to vary in consistency from a soft wax to a paste. Such consistency is important for subsequent handling of the product, including the ease with which it will disperse in aqueous systems to be thickened by it. While on a laboratory scale it is possible to control consistency of the higher molecular weight products merely by including more solvent during synthesis, production scale normally requires minimal use of a non-polar solvent during synthesis to maintain kettle capacity, followed by addition of a softening agent to the mixture towards the end of or following synthesis.

Although certain polar solvents may also be present during synthesis (those which are inert to isocyanate, such as ketones and esters), such presence is not preferred because of solvent recovery cost, the difficulty of keeping polar solvents moisture-free, and phase separation. Preferably, product consistency is controlled by synthesizing the higher molecular weight products in the presence of a non-polar solvent and then adding the softening agent to the reaction product mixture. A useful softening agent is a polar or non-polar organic solvent, a nonionic surfactant such as a polyethoxylated alkyl phenol, or any mixtures of two or more of such solvents and/or surfactants. The product may be isolated prior to treatment with the softening agent but there is usually no advantage to this due to increased process cost.

The amount of softening agent may vary widely, for example on the order of about 1–50% by weight of the reaction product mixture, and preferably is about 2–15% by weight. The softening agent may also include a minor amount of water, on the order of about 0.5–10%, preferably about 1–2%, based on total reaction product mixture weight. The preferred softening agents are mixtures of nonpolar aromatic hydrocarbon solvents and polar organic solvents, with or without water, such as the reaction medium solvents mentioned above. Typical mixtures and amounts effective for softening the polyurethane products include the following, where the "Solvesso" (trademark) 100 nonpolar aromatic solvent may be added as part of the softener or may already be present in the reaction product mixture, and the polyurethane reaction product mixture is at about 80° C. during softener addition:

| SOFTENER | WT. % ON POLYURETHANE PRODUCT |
| --- | --- |
| Solvesso 100/isopropanol | 50/5–10 |
| Solvesso 100/ethanol | 50/5 |
| Solvesso 100/n-butanol | 50/5 |
| Solvesso 100/t-butanol | 50/5–10 |
| Solvesso 100/n-butanol/water | 50/5–10/2 |
| Solvesso 100/butyl Cellosolve | 50/10 |
| Solvesso 100/butyl Cellosolve/water | 50/10/2 |

LATEX PAINT COMPOSITIONS

The invention includes latex paint compositions containing an emulsion or dispersion of a water-insoluble polymer and a polymeric thickener of the foregoing polymer groups. The water-insoluble polymers may be any of the types conventionally utilized in latex paint compositions and include natural rubber latex ingredients and synthetic latices wherein the water-insoluble polymer is an emulsion polymer of mono- or polyethylenically unsaturated olefinic, vinyl or acrylic monomer types, including homopolymers and copolymers of such monomers. Specifically, the water-insoluble emulsion polymer may include poly(vinyl acetate) and copolymers of vinyl acetate (preferably at least 50% by weight) with one or more of vinyl chloride, vinylidene chloride, styrene, vinyltoluene, acrylonitrile, methacrylonitrile, acrylamide, methacrylamide, maleic acid and esters thereof, or one or more of the acrylic and methacrylic acid esters mentioned in U.S. Pat. Nos. 2,795,564 and 3,356,627, which polymers are well-known as the film-forming component of aqueous base paints; homopolymers of $C_2$–$C_{40}$ alpha olefins such as ethylene, isobutylene, octene, nonene, and styrene, and the like; copolymers of one or more of these hydrocarbons with one or more esters, nitriles or amides of acrylic acid or of methacrylic acid or with vinyl esters, such as vinyl acetate and vinyl chloride, or with vinylidene chloride; and diene polymers, such as copolymers of butadiene with one or more of styrene, vinyl toluene, acylonitrile, methacrylonitrile, and esters of acrylic acid or methacrylic acid. It is also quite common to include a small amount, such as 0.5 to 2.5% or more, of an acid monomer in the monomer mixture used for making the copolymers mentioned above by emulsion polymerization. Acids used include acrylic, methacrylic, itaconic, aconitic, citraconic, crotonic, maleic, fumaric, the dimer of methacylic acid, and so on.

The vinyl acetate copolymers are well-known and include copolymers such as vinyl acetate/butyl acrylate/2-ethylhexyl acrylate, vinyl acetate/butyl maleate, vinyl acetate/ethylene, vinyl acetate/vinyl chloride/butyl acrylate and vinyl acetate/vinyl chloride/ethylene.

Throughout this specification the term "acrylic polymer" means any polymer wherein at least 50% by weight is an acrylic or methacrylic acid or ester, including mixtures of such acids and esters individually and together. The term "vinyl acetate polymer" means any polymer containing at least 50% by weight of vinyl acetate.

Even small particle size (about 0.1–0.15 micron) acrylic and other latices are thickened effectively, and flow and leveling improved, by thickeners of the invention. Such latices are notoriously resistant to improvement with conventional thickeners.

The aqueous polymer dispersions may be prepared according to well known procedures, using one or more emulsifiers of an anionic, cationic, or nonionic type. Mixtures of two or more emulsifiers regardless of type may be used, except that it is generally undesirable to mix a cationic with an anionic type in any appreciable amounts since they tend to neutralize each other. The amount of emulsifier may range from about 0.1 to 6% by weight or sometimes even more, based on the weight of the total monomer charge. When using a persulfate type of initiator, the addition of emulsifiers is often necessary. This omission or the use of only a small amount, e.g., less than about 0.5%, of emulsifier, may sometimes be desirable from a cost standpoint, and less sensitivity of the dried coating or impregnation to moisture, and hence less liability of the coated substrate to be affected by moisture. In general, the molecular weight of these emulsion polymers is high, e.g., from about 100,000 to 10,000,000 viscosity average, most commonly above 500,000.

The foregoing and other emulsion polymer systems which may be thickened with the polymeric thickeners of the invention are set forth in the extensive literature on the subject, such as U.S. Pat. Nos. 3,035,004; 2,795,564; 2,875,166 and 3,037,952, for example. The polymeric thickeners are also suitable or substitutes for the polmeric thickeners in the polymeric systems disclosed in U.S. Pat. Nos. 2,875,166 and 3,035,004 and in Canadian Pat. No. 623,617.

One of the outstanding benefits when using the polymeric thickeners of the invention is the capability of "fine tuning" the structure of the polymers to obtain optimum values and balance of viscosity in aqueous dispersions containing the polymers, under high and low shear conditions, as well as film building ability, flow and leveling, and other properties especially desirable in latex paint compositions. This is achieved by building into the polymeric thickener specific types and sizes of hydrophobic groups and by selecting hydrophil molecular weight so as to provide inter-hydrophobe distances effective for good thickening by an associative mechanism. The hydrophobic groups which lend themselves most readily to such control are the terminal hydrophobic groups preferably containing about 4–20 carbon atoms based on aliphatic or aromatic monohydroxy or monoamino compounds (alcohols, phenols, amines) and organic monoisocyanates. It is especially surprising that such control can be effected with small, relatively low molecular weight hydrophobic capping groups.

The polymeric thickeners may be added to polymer latex systems at any time during the preparation thereof, including during or after polymerization or copolymerization and by single or multiple additions. Normally, from about 0.1% to about 10%, preferably 1–3%, by weight of polymeric thickener on polymer latex solids is adequate to provide suitable levels of thickening and other properties. However, the amount may be higher or lower depending on the particular system, other additives present, and similar reasons understood by the formulator.

Since the polymeric thickeners are nonionic they are especially useful in latex paint and other latex compositions having an alkaline pH. They are also compatible with a great variety of latex composition additives such as defoaming agents, pigment dispersants, and surfactants of all types, and permit extended shelf life. The thickeners may be admixed with other components of the paint or other composition at any point during manufacture thereof and may even be the final addition to the composition. From the standpoint of capability of tailoring the thickeners to obtain an optimum balance of properties in paint compositions and from the standpoint of resistance to degradation, the polymeric thickeners offer substantial advantages over natural or semisynthetic thickening agents such as hydroxyethyl cellulose, casein, alginates and starches.

OTHER APPLICATIONS

Other aqueous systems in which the polymeric thickeners are useful include aqueous coating compositions for the paper, leather and textile industries, oil well flooding compositions and drilling muds, detergents, adhesives, waxes, polishes, cosmetics and toiletries, topical pharmaceuticals, and pesticidal or agricultural compositions for the control of insects, rodents, fungi, parasites of all kinds, and undesirable plant growth.

Moreover, the polymers are useful for the thickening of water alone, the resulting solution then being useful for addition to another system to be thickened. For example, the addition of a suitable amount of a water soluble alcohol such as methanol to a water solution containing 25% by weight of the thickener forms a "clear concentrate" useful in preparing pigment printing pastes.

In the textile field the thickeners are useful in warp sizes, textile finishes, bonding agents for both wovens and non-wovens, tie-coats, and for the thickening of dyeing and coloring compositions of all types. For printing paste emulsions and dispersions it has been found that the Group B and C polymers (Examples 103–225) perform better than the linear polymers of Group A, possibly because the Group B and C polymers contain more hydrophobic groups and/or higher molecular weight hydrophobic groups. The textile printing pastes may be simple aqueous dispersion or oil-in-water emulsions. Any water soluble or insoluble coloring material may be used, such as inorganic pigments and vat dyes. For example, thickeners of the invention may be used as substitutes for the thickeners disclosed in the dyestuff or coloring assistant compositions of U.S. Pat. Nos. 3,468,620; 3,467,620; 3,467,485 and 3,391,985.

Although an organic isocyanate is an essential reactant in forming the polymeric thickeners of the invention, any residual isocyanate is easily eliminated by dispersing the thickeners in water. This removes any isocyanate toxicity from the thickeners and thereby makes them suitable as additives to various types of cosmetics such as hand creams, hand lotions, cleansing creams, hair creams, cold waving lotions, shampoos, creme rinses and the like. The thickeners of the invention also form "ringing" gels in aqueous solution in the manner of the polyoxyethylene-polyoxypropylene gels of U.S. Pat. No. 3,740,421 and can be used in cosmetic and pharmaceutical compositions similar to the gels of that patent.

The following examples will further illustrate the invention in one or more of its various aspects. Examples 4–10 (which describe polymers of formula I above where n is 1) while not representative of polymers believed to be patentable per se, illustrate other inventive aspects, such as use in the polymer emulsion and latex paint embodiments which begin with Example 226. All parts and percentages in the Examples are by weight unless otherwise indicated. Molecular weights of polyalkylene ether reactants or residues are by hydroxyl number unless otherwise indicated.

EXAMPLES 1–102

Group A—Linear Polymers

EXAMPLE 1

Tolylene diisocyanate (TDI)—polyethylene glycol (PEG) prepolymer capped with dodecyl isocyanate A mixture of 60 g. of PEG (molecular weight 6000) and 200 g. of toluene was dried by azeotropic distillation. The mixture was cooled to 75° C., and 0.06 g. of dibutyltin dilaurate and 1.4 g. of TDI was added. After 2 hours at 75° C., 1.7 g. of dodecyl isocyanate was added. The mixture was then maintained at 60° C. for 4 days. The resulting solid polymer, isolated after toluene evaporation from a slab mold, had a gel permeation chromatogram indicating a weight average molecular weight (Mw) of 71,100 and a number average molecular weight (Mn) of 15,900.

EXAMPLES 2 AND 3

TDI-PEG prepolymer capped with dodecyl isocyanate and octadecyl isocyanate

A mixture of 400 g. of PEG (molecular weight 4000) and about 600 g. of toluene was dried by azeotropic distillation. The mixture was cooled to 75° C. and 0.4 g. of dibutyltin dilaurate was added. To one-third of this reaction mixture was added 6.34 g. of dodecyl isocyanate (Example 2). To another third of the reaction mixture was added 8.9 g. of octadecyl isocyanate (Example 3). The solid polymeric products were isolated as described in Example 1.

The structures of the polymeric products of Examples 1–3 are set forth below in conjunction with Table 1. This table also includes similar products prepared essentially as the foregoing with the major variations as indicated.

Table 1

$$\text{R}-\overset{\text{H}}{\underset{|}{\text{N}}}-\overset{\text{O}}{\underset{\|}{\text{C}}}-(\text{OCH}_2\text{CH}_2)_x\!\!\left[\text{O}-\overset{\text{O}}{\underset{\|}{\text{C}}}-\overset{\text{H}}{\underset{|}{\text{N}}}-\text{R}''-\overset{\text{H}}{\underset{|}{\text{N}}}-\overset{\text{O}}{\underset{\|}{\text{C}}}-(\text{OCH}_2\text{CH}_2)_x\right]_n\!\!\text{O}-\overset{\text{O}}{\underset{\|}{\text{C}}}-\overset{\text{H}}{\underset{|}{\text{N}}}-\text{R}'$$

| Ex. No. | R | R' | R'' | x | n |
|---|---|---|---|---|---|
| 1 | n-$C_{12}H_{25}$ | n-$C_{12}H_{25}$ | [1]/$C_7H_6$ | 136 | 3 |
| 2 | n-$C_{12}H_{25}$ | n-$C_{12}H_{25}$ | $C_7H_6$ | 91 | 2 |
| 3 | n-$C_{18}H_{37}$ | n-$C_{12}H_{25}$ | $C_7H_6$ | 91 | 2 |
| 4 | n-$C_{18}H_{37}$ | n-$C_{18}H_{37}$ | [2]/$C_{36}$ based | 455 | 1 |
| 5 | n-$C_{18}H_{37}$ | n-$C_{18}H_{37}$ | [3]/$C_{13}H_{22}$ | 455 | 1 |
| 6 | n-$C_{18}H_{37}$ | n-$C_{18}H_{37}$ | $C_7H_6$ | 455 | 1 |
| 7 | n-$C_8H_{17}$ | n-$C_8H_{17}$ | $C_{36}$ based | 136 | 1 |
| 8 | n-$C_{18}H_{37}$ | n-$C_{18}H_{37}$ | $C_{36}$ based | 136 | 1 |
| 9 | n-$C_{18}H_{37}$ | n-$C_{18}H_{37}$ | $C_{13}H_{22}$ | 136 | 1 |
| 10 | n-$C_{12}H_{25}$ | n-$C_{12}H_{25}$ | $C_{13}H_{22}$ | 136 | 1 |
| 11 | n-$C_{18}H_{37}$ | n-$C_{18}H_{37}$ | $C_7H_6$ | 136 | 2 |
| 12 | n-$C_{12}H_{25}$ | n-$C_{12}H_{25}$ | $C_{13}H_{22}$ | 136 | 2 |
| 13 | n-$C_{18}H_{37}$ | n-$C_{18}H_{37}$ | $C_{13}H_{22}$ | 136 | 2 |
| 14 | n-$C_{12}H_{25}$ | n-$C_{12}H_{25}$ | $C_{13}H_{22}$ | 136 | 4 |
| 15 | n-$C_{12}H_{25}$ | n-$C_{12}H_{25}$ | $C_{13}H_{22}$ | 136 | 4 |
| 16 | n-$C_{18}H_{37}$ | n-$C_{18}H_{37}$ | $C_7H_6$ | 136 | 4 |
| 17 | n-$C_{18}H_{37}$ | n-$C_{12}H_{25}$ | $C_7H_6$ | 136 | 4 |

Table 1-continued $$\text{R}-\overset{\text{H}}{\underset{|}{\text{N}}}-\overset{\text{O}}{\underset{\|}{\text{C}}}-(\text{OCH}_2\text{CH}_2)_x\!\!\left[\!\!-\text{O}-\overset{\text{O}}{\underset{\|}{\text{C}}}-\overset{\text{H}}{\underset{|}{\text{N}}}-\text{R}'''-\overset{\text{H}}{\underset{|}{\text{N}}}-\overset{\text{O}}{\underset{\|}{\text{C}}}-(\text{OCH}_2\text{CH}_2)_x\!\right]_{\!\!n}\!\!\text{O}-\overset{\text{O}}{\underset{\|}{\text{C}}}-\overset{\text{H}}{\underset{|}{\text{N}}}-\text{R}'$$

| Ex. No. | R | R' | R'' | x | n |
|---|---|---|---|---|---|
| 17A | n-$C_{18}H_{37}$ | n-$C_{18}H_{37}$ | $C_7H_6$ | 136 | 3 |

[1] The diisocyanate providing this residue throughout all examples of this application was a commercial mixture of the 2,4- and 2,6-isomers of tolylene diisocyanate. The value of x in all examples is based on the nominal molecular weights of commercial polyethylene glycol products rather than on assay of each lot.

[2] The diisocyanate providing this residue throughout all examples of this application was "DDI", a $C_{36}$ dimer acid-based diisocyanate from General Mills Corporation.

[3] The diisocyanate providing this residue throughout all examples of this application was 4,4'-methylenebis-(isocyanatocyclohexane), commercially available as "Hylene W".

EXAMPLES 18–74T

Isocyanate terminated prepolymers of polyoxyethylene glycol and diisocyanates capped with aliphatic alcohols or amines The reactions tabulated in Table 2 below were conducted by predrying a mixture of 50 g. of PEG (4000 to 20,000 molecular weight), 0.05 g. of dibutyltin dilaurate and 50 g. of toluene by azeotropic distillation. The reaction mixture was cooled to 60° C., and an aliphatic alcohol or amine was added, followed by the diisocyanate listed. The reaction temperature was maintained at 60° C. for 3–5 days before isolation of the solid polymer by evaporation of the solid thickener in a slab mold. The structures of the products are set forth below in conjunction with Table 2.

Table 2

$$\text{R}-\text{O}\!\!\left[\!\!-\overset{\text{O}}{\underset{\|}{\text{C}}}-\overset{\text{H}}{\underset{|}{\text{N}}}-\text{R}'''-\overset{\text{H}}{\underset{|}{\text{N}}}-\overset{\text{O}}{\underset{\|}{\text{C}}}-\text{O}-(\text{CH}_2\text{CH}_2\text{O})_x\!\right]_{\!\!n}\!\!\overset{\text{O}}{\underset{\|}{\text{C}}}-\overset{\text{H}}{\underset{|}{\text{N}}}-\text{R}'''-\overset{\text{H}}{\underset{|}{\text{N}}}-\overset{\text{O}}{\underset{\|}{\text{C}}}-\text{O}-\text{R}$$

$$\text{R}'-\overset{}{\underset{\text{R}''}{\text{N}}}\!\!\left[\!\!-\overset{\text{O}}{\underset{\|}{\text{C}}}-\overset{\text{H}}{\underset{|}{\text{N}}}-\text{R}'''-\overset{\text{H}}{\underset{|}{\text{N}}}-\overset{\text{O}}{\underset{\|}{\text{C}}}-\text{O}-(\text{CH}_2\text{CH}_2\text{O})_x\!\right]_{\!\!n}\!\!\overset{\text{O}}{\underset{\|}{\text{C}}}-\overset{\text{H}}{\underset{|}{\text{N}}}-\text{R}'''-\overset{\text{H}}{\underset{|}{\text{N}}}-\overset{\text{O}}{\underset{\|}{\text{C}}}-\overset{}{\underset{\text{R}''}{\text{N}}}-\text{R}'$$

| Ex. No. | R | R' | R'' | R''' | x | n |
|---|---|---|---|---|---|---|
| 18 | n-$C_8H_{17}$ | — | — | $C_{13}H_{22}$[1] | 455 | 1 |
| 19 | n-$C_{12}H_{25}$ | — | — | $C_{13}H_{22}$ | 455 | 1 |
| 20 | n-$C_8H_{17}$ | — | — | $C_7H_6$ | 136 | 1 |
| 21 | n-$C_{12}H_{25}$ | — | — | $C_7H_6$ | 136 | 1 |
| 22 | n-$C_{18}H_{37}$ | — | — | $C_7H_6$ | 136 | 1 |
| 23 | n-$C_8H_{17}$ | — | — | $C_7H_6$ | 136 | 2 |
| 24 | n-$C_{12}H_{25}$ | — | — | $C_7H_6$ | 136 | 2 |
| 25 | n-$C_{18}H_{37}$ | — | — | $C_7H_6$ | 136 | 2 |
| 26 | n-$C_4H_9$ | — | — | $C_{13}H_{22}$ | 136 | 1 |
| 27 | t-octylphenol | — | — | $C_{13}H_{22}$ | 136 | 1 |
| 28 | — | H | t-$C_{12}H_{25}$ | $C_{13}H_{22}$ | 136 | 1 |
| 29 | — | H | t-$C_8H_{17}$ | $C_7H_6$ | 136 | 1 |
| 30 | n-$C_{12}H_{25}$ | — | — | $C_7H_6$ | 136 | 1 |
| 31 | t-octylphenyl | — | — | $C_7H_6$ | 136 | 1 |
| 32 | n-$C_8H_{17}$ | — | — | $C_{13}H_{22}$ | 136 | 2 |
| 33 | — | H | t-$C_{12}H_{25}$ | $C_{13}H_{22}$ | 136 | 2 |
| 34 | n-$C_{14}H_{29}$ | — | — | $C_7H_6$ | 136 | 1 |
| 35 | n-$C_8H_{17}$ | — | — | $C_7H_6$ | 136 | 4 |
| 36 | $C_{16}H_{33}$ | — | — | $C_7H_6$ | 136 | 4 |
| 37 | $C_{12}H_{25}$ | — | — | $C_7H_6$ | 136 | 5 |
| 38 | $C_{12}H_{25}$ | — | — | $C_7H_6$ | 136 | 3 |
| 39 | $C_4H_9$ | — | — | $C_{13}H_{22}$ | 136 | 4 |
| 40 | $C_8H_{17}$ | — | — | $C_{13}H_{22}$ | 136 | 5 |
| 41 | $C_{18}H_{37}$ | — | — | $C_7H_6$ | 136 | 2.5 |
| 42 | $C_{18}H_{37}$ | — | — | $C_7H_6$ | 136 | 1.5 |
| 43 | $C_{18}H_{37}$ | — | — | $C_7H_6$ | 136 | 10 |
| 44 | $C_{12}H_{25}$ | — | — | $C_7H_6$ | 163 | 4 |
| 45 | $C_{12}H_{25}$ | — | — | $C_7H_6$ | 163 | 8 |
| 46 | H | — | — | $C_7H_6$ | 163 | 4 |
| 47 | $C_{12}H_{25}$ | — | — | $C_7H_6$ | 163 | 18 |
| 48 | $C_{12}H_{25}$ | — | — | $C_7H_6$ | 218 | 4 |
| 49 | $C_{12}H_{25}$ | — | — | $C_7H_6$ | 386 | 4 |
| 50 | $C_{12}H_{25}$ | — | — | $C_7H_6$ | 386 | 8 |
| 51 | $C_8H_{17}$ | — | — | $C_{13}H_{22}$ | 163 | 4 |
| 52 | $C_8H_{17}$ | — | — | $C_{13}H_{22}$ | 163 | 8 |
| 53 | $C_{10}H_{21}$ | — | — | $C_7H_6$ | 163 | 8 |
| 54 | $C_{10}H_{21}$ | — | — | $C_7H_6$ | 163 | 4 |
| 55 | $C_{10}H_{21}$ | — | — | $C_7H_6$ | 163 | 2 |
| 56 | $C_{14}H_{29}$ | — | — | $C_7H_6$ | 163 | 1.5 |
| 57 | $C_{12}H_{25}$ | — | — | $C_7H_6$ | 163 | 2 |
| 58 | $C_{12}H_{25}$ | — | — | $C_7H_6$ | 163 | 1 |
| 59 | $C_{12}H_{25}$ | — | — | $C_7H_6$ | 163 | 8 |
| 60 | $C_{12}H_{25}$ | — | — | $C_7H_6$ | 163 | 4 |
| 61 | $C_{12}H_{25}$ | — | — | $C_7H_6$ | 163 | 2 |
| 62 | — | t-dodecyl | H | $C_7H_6$ | 163 | 8 |
| 63 | — | t-dodecyl | H | $C_7H_6$ | 163 | 4 |
| 64 | — | t-dodecyl | H | $C_7H_6$ | 163 | 2 |
| 65 | — | t-$C_{18}H_{37}$ | H | $C_7H_6$ | 163 | 8 |

Table 2-continued $$R-O+\overset{O}{\underset{\|}{C}}-\overset{H}{\underset{|}{N}}-R'''-\overset{H}{\underset{|}{N}}-\overset{O}{\underset{\|}{C}}-O-(CH_2CH_2O)_x\overset{}{\underset{}{\big]}}_n\overset{O}{\underset{\|}{C}}-\overset{H}{\underset{|}{N}}-R'''-\overset{H}{\underset{|}{N}}-\overset{O}{\underset{\|}{C}}-O-R$$

$$R'-\overset{}{\underset{|}{N}}+\overset{O}{\underset{\|}{C}}-\overset{H}{\underset{|}{N}}-R'''-\overset{H}{\underset{|}{N}}-\overset{O}{\underset{\|}{C}}-O-(CH_2CH_2O)_x\overset{}{\underset{}{\big]}}_n\overset{O}{\underset{\|}{C}}-\overset{H}{\underset{|}{N}}-R'''-\overset{H}{\underset{|}{N}}-\overset{O}{\underset{\|}{C}}-\overset{}{\underset{|}{N}}-R'$$
$$R''\qquad\qquad\qquad\qquad\qquad\qquad\qquad\qquad R''$$

| Ex. No. | R | R' | R'' | R''' | x | n |
|---|---|---|---|---|---|---|
| 66 | — | " | H | " | 163 | 4 |
| 67 | — | " | H | " | 163 | 2 |
| 68 | — | t-octyl | H | $C_{13}H_{22}$ | 163 | 8 |
| 69 | — | " | H | " | 163 | 4 |
| 70 | — | " | H | " | 163 | 2 |
| 71 | — | t-dodecyl | H | " | 163 | 8 |
| 72 | — | t-dodecyl | H | $C_{13}H_{22}$ | 163 | 4 |
| 73 | $C_8H_{17}$ | — | — | " | 163 | 4 |
| 74 | — | t-dodecyl | H | " | 163 | 2 |
| 74A | $C_{12}H_{25}$ | — | — | $C_7H_6$ | 170 | 4 |
| 74B | menthol | — | — | " | 136 | 4 |
| 74C | dicyclopentenyl | — | — | " | 136 | 4 |
| 74D | benzhydrol | — | — | " | 136 | 4 |
| 74E | — | benzyl | benzyl | " | 136 | 4 |
| 74F | — | " | " | $C_{13}H_{22}$ | 136 | 4 |
| 74G | — | phenyl | phenyl | $C_7H_6$ | 136 | 4 |
| 74H | — | " | " | $C_{13}H_{22}$ | 136 | 4 |
| 74I | — | cyclohexyl | cyclohexyl | $C_7H_6$ | 136 | 4 |
| 74J | — | " | " | $C_{13}H_{22}$ | 136 | 4 |
| 74K | $C_{12}H_{25}$ | — | — | $C_{13}H_{10}$[2] | 136 | 4 |
| 74L | " | — | — | " | 136 | 3 |
| 74M | " | — | — | $C_6H_{12}$[3] | 136 | 4 |
| 74N | $C_{12}H_{25}$ | — | — | $C_{13}H_{10}$ | 173 | 4 |
| 74O | $C_{14}H_{29}$ | — | — | $C_{13}H_{10}$ | 173 | 8 |
| 74P | $C_{16}H_{33}$ | — | — | " | 173 | 8 |
| 74Q | $C_{18}H_{37}$ | — | — | " | 173 | 8 |
| 74R | $C_{20}H_{41}$ | — | — | " | 173 | 8 |
| 74S | $C_{20}H_{41}$ | — | — | $C_{13}H_{22}$ | 173 | 8 |
| 74T | $C_{20}H_{41}$ | — | — | $C_7H_6$ | 173 | 8 |

[1] residue of "Hylene W" diisocyanate
[2] residue of MDI
[3] residue of HDI

EXAMPLES 75–96

Diisocyanate-polyethylene glycol prepolymers capped with ethylene oxide-monohydric compound adducts A mixture of 600 g. of dried PEG (6000 molecular weight), 0.6 g. of dibutyltin dilaurate, and 26.1 g. of tolylene diisocyanate was allowed to react at 60° C. for 24 hours. At that time, the toluene solution was split into six equal portions; to four of these was separately added 15 milliequivalents of a predried alcohol of structure (a) octylphenol-ethylene oxide adduct of molecular weight 3000, (b) hexadecyl alcohol-ethylene oxide adduct of molecular weight 3000, (c) dodecyl alcohol-ethylene oxide adduct of 2600 molecular weight, and (d) octadecanol-ethylene oxide adduct of 2800 molecular weight. The reaction temperature of 60° C. was maintained for four days, and the solutions were poured out to air dry. The resulting polymers have the structure indicated below and in Table 3 (Examples 75, 77, 78 and 79, respectively). The Table includes other polymers prepared in essentially the same manner.

Table 3

$$R-O+CH_2CH_2O\overset{}{\underset{}{\big]}}_x\overset{O}{\underset{\|}{C}}-\overset{H}{\underset{|}{N}}-R'-\overset{H}{\underset{|}{N}}-\overset{O}{\underset{\|}{C}}-O-(CH_2CH_2-O)_y\overset{}{\underset{}{\big]}}_n\overset{O}{\underset{\|}{C}}-\overset{H}{\underset{|}{N}}-R'N-\overset{O}{\underset{\|}{C}}+OCH_2CH_2\overset{}{\underset{}{\big]}}_xOR$$

| Ex. No. | R | R' | x | y | n |
|---|---|---|---|---|---|
| 75 | t-octylphenyl | $C_7H_6$ | 62 | 136 | 1 |
| 76 | n-$C_{12}H_{25}$ | $C_{13}H_{22}$ | 105 | 136 | 2 |
| 77 | n-$C_{16}H_{33}$ | $C_7H_6$ | 62 | 136 | 1 |
| 78 | n-$C_{12}H_{25}$ | $C_7H_6$ | 51 | 136 | 1 |
| 79 | n-$C_{18}H_{37}$ | $C_7H_6$ | 59 | 136 | 1 |
| 80 | t-octylphenyl | $C_{13}H_{22}$ | 62 | 136 | 1 |
| 81 | n-$C_{18}H_{37}$ | $C_{13}H_{22}$ | 59 | 136 | 1 |
| 82 | n-$C_{14}H_{29}$ | $C_7H_6$ | 93 | 136 | 2 |
| 83 | n-$C_{14}H_{29}$ | $C_7H_6$ | 166 | 136 | 2 |
| 84 | $C_{12}H_{25}$ | $C_7H_6$ | 105 | 136 | 4 |
| 85 | $C_{14}H_{29}$ | $C_7H_6$ | 100 | 136 | 4 |
| 86 | $C_{12}H_{25}$ | $C_7H_6$ | 105 | 136 | 3 |
| 87 | $C_{12}H_{25}$ | $C_7H_6$ | 105 | 136 | 8 |
| 88 | $C_{12}H_{25}$ | $C_7H_6$ | 105 | 136 | 4 |
| 89 | $C_{12}H_{25}$ | $C_{13}H_{22}$ | 105 | 136 | 8 |
| 90 | $C_{12}H_{25}$ | $C_{13}H_{22}$ | 105 | 136 | 4 |
| 91 | $C_{12}H_{25}$ | $C_7H_6$ | 51 | 136 | 4 |
| 92 | t-octylphenyl | $C_7H_6$ | 101 | 136 | 4 |
| 93 | $C_{16}H_{33}$ | $C_7H_6$ | 223 | 1 | 2 |

Table 3-continued $$R-O(CH_2CH_2O)_x[\overset{O}{\overset{\|}{C}}-\overset{H}{\overset{|}{N}}-R'-\overset{H}{\overset{|}{N}}-\overset{O}{\overset{\|}{C}}-O-(CH_2CH_2-O)_y]_n\overset{O}{\overset{\|}{C}}-\overset{H}{\overset{|}{N}}-R'\overset{H}{\overset{|}{N}}-\overset{O}{\overset{\|}{C}}(OCH_2CH_2)_x OR$$

| Ex. No. | R | R' | x | y | n |
|---|---|---|---|---|---|
| 94 | $C_{16}H_{33}$ | $C_7H_6$ | 223 | 1 | 1 |
| 95 | $C_{12}H_{25}$ | $C_7H_6$ | 137 | 9 | 1 |
| 96 | $C_{16}H_{33}$ | $C_7H_6$ | 223 | 9 | 1 |
| 96A | $C_{12}H_{25}$ | $C_7H_6$ | 105 | 136 | 2 |
| 96B | $C_{12}H_{25}$ | $C_7H_6$ | 105 | 136 | 1 |

EXAMPLES 97–102

Polyethylene glycol-diisocyanate prepolymers reacted with diisocyanate and capped with monohydric alcohol A mixture of 120 g. of PEG (20,000 molecular weight), 480 g. of toluene, and 0.12 g. of dibutyltin dilaurate were dried by azeotropic distillation. At 75° C., 2.16 g. of "DDI" diisocyanate was added. In two hours (at 75° C.), 2.2 g. of 4,4'-biscyclohexylmethane diisocyanate was added, and the reaction mixture was stored at 60° C. for 3 days. The mixture was then split into three equal parts. To mixture A was added 0.355 g. of n-butanol, to mixture B was added 0.625 g. of n-octanol, and to mixture C was added 0.90 g. of n-dodecanol. After 4 days at 60° C., the samples were poured out to air dry. The polymeric products have the following structure as further defined in Examples 97–99 of Table 4 together with other products prepared in substantially the same manner.

tially the same manner as the Example 103 product, with the major variations as indicated in the Table.

Table 5

$$CH_3CH_2-C[CH_2O-(CH_2CH_2O)_x-\overset{O}{\overset{\|}{C}}-\overset{H}{\overset{|}{N}}-R]_3$$

| Ex. No. | R | x | Equivalents NCO/OH |
|---|---|---|---|
| 103 | n-$C_{18}H_{37}$ | 102 | 1.37/1 |
| 104 | " | 104 | 0.43/1 |
| 105 | " | 34 | 1.35/1 |
| 106 | " | 73 | 0.87/1 |
| 107 | " | 53 | 1.05/1 |
| 108 | " | 53 | 0.7/1 |
| 109 | " | 102 | 1/1 |
| 110 | " | 53 | 1/1 |
| 111 | n-$C_{12}H_{25}$ | 132 | 1.2/1 |
| 112 | n-$C_8H_{17}$ | 142 | 1.2/1 |
| 113 | n-$C_{12}H_{25}$ | 73 | 0.9/1 |
| 114 | " | 73 | 1.1/1 |
| 115 | n-$C_{18}H_{37}$ | 132 | 1.2/1 |

$$R-O-\overset{O}{\overset{\|}{C}}-\overset{H}{\overset{|}{N}}-R''-\overset{H}{\overset{|}{N}}-\overset{O}{\overset{\|}{C}}(OCH_2CH_2)_x-O-\overset{O}{\overset{\|}{C}}-\overset{H}{\overset{|}{N}}-R'''-\overset{H}{\overset{|}{N}}-\overset{O}{\overset{\|}{C}}]_n-O-(CH_2CH_2-O)_x\overset{O}{\overset{\|}{C}}-\overset{H}{\overset{|}{N}}-R''-\overset{H}{\overset{|}{N}}-\overset{O}{\overset{\|}{C}}-O-R$$

| Ex. No. | R | R''' | R'' | x | n |
|---|---|---|---|---|---|
| 97 | n-$C_4H_9$ | $C_{36}$ based | $C_{13}H_{22}$ | 455 | 1 |
| 98 | n-$C_8H_{17}$ | $C_{36}$ based | $C_{13}H_{22}$ | 455 | 1 |
| 99 | n-$C_{12}H_{25}$ | $C_{36}$ based | $C_{13}H_{22}$ | 455 | 1 |
| 100 | n-$C_8H_{17}$ | $C_{36}$ based | $C_7H_6$ | 455 | 1 |
| 101 | n-$C_{12}H_{25}$ | $C_{36}$ based | $C_7H_6$ | 455 | 1 |
| 102 | n-$C_{18}H_{37}$ | $C_{36}$ based | $C_7H_6$ | 455 | 1 |

EXAMPLES 103–153

Group B—Star-Shaped Polymers

EXAMPLE 103

Trimethylolpropane-ethylene oxide adduct capped with octadecyl isocyanate

In a suitable reaction vessel 70 g. of trimethylolpropane-ethylene oxide adduct with a hydroxyl number of 12.5 (eq. wt. 4500 per OH) and about 100 g. of toluene were dried by azeotropic distillation. Then 0.07 g. of dibutyltin dilaurate and 6.34 g. of octadecyl isocyanate was added. After 4 days at 60° C., the sample was dried in a slab mold. The structure of this polymeric product is set forth below in conjunction with Table 5 which also lists similar polymeric products prepared in essen-

EXAMPLES 116–140A

Triisocyanate coupled with ethoxylated dodecanol and methoxy capped-polyethylene glycol Two mixtures of 40 g. each of ethoxylated dodecanol of 7300 molecular weight, 11.8 g. of monomethoxy capped-polyethylene glycol of 5000 molecular weight, 80 g. of toluene and 0.08 g. of dibutyltin dilaurate were dried by azeotropic distillation. After cooling to 60° C., 2.54 g. of Mondur CB-75 (Example 116) or 2.09 g. of Desmodur N (Example 117) were added to the reaction mixtures. After 3 hours at 60° C., the infrared spectrum indicated complete reaction, and the reaction mixtures were poured into slab molds to isolate the solid polymers. The structures of these and other polymers, prepared in essentially the same manner, are given below in conjunction with Table 6.

Table 6

$$[R(R')(R'')-O-(CH_2CH_2-O)_{x\overline{(x')}}\overset{O}{\overset{\|}{C}}_{\overline{(x'')}}\overset{H}{\overset{|}{N}}]_n R'''$$

| Ex. No. | R | R' | R'' | R''' | x | x' | x'' | n |
|---|---|---|---|---|---|---|---|---|
| 116 | n-$C_{12}H_{25}$ | $CH_3$ | n-$C_{12}H_{25}$ | $C_{30}$[1] | 162 | 113 | 162 | 3 |
| 117 | " | " | " | $C_{20}$[2] | 162 | 113 | 162 | 3 |
| 118 | " | n-$C_{12}H_{25}$ | " | $C_{20}$ | 55 | 55 | 55 | 3 |
| 119 | " | " | " | $C_{20}$ | 105 | 105 | 105 | 3 |
| 120 | " | " | " | $C_{20}$ | 159 | 159 | 159 | 3 |

Table 6-continued $$[R(R')(R'')-O-(CH_2CH_2-O)_{x\overline{(x')}}\underset{\underset{H}{|}}{\overset{\overset{O}{\|}}{C}}_{\overline{(x'')}}N]_n R'''$$

| Ex. No. | R | R' | R'' | R''' | x | x' | x'' | n |
|---|---|---|---|---|---|---|---|---|
| 121 | n-$C_{14}H_{29}$ | n-$C_{14}H_{29}$ | n-$C_{14}H_{29}$ | $C_{20}$ | 114 | 114 | 114 | 3 |
| 122 | n-$C_{16}H_{33}$ | n-$C_{16}H_{33}$ | n-$C_{16}H_{33}$ | $C_{20}$ | 139 | 139 | 139 | 3 |
| 123 | n-$C_{18}H_{37}$ | n-$C_{18}H_{37}$ | n-$C_{18}H_{37}$ | $C_{20}$ | 142 | 142 | 142 | 3 |
| 124 | t-octyl phenyl | t-octyl phenyl | t-octyl phenyl | $C_{20}$ | 166 | 166 | 166 | 3 |
| 125 | n-$C_{12}H_{25}$ | $CH_3$ | n-$C_{12}H_{25}$ | $C_{20}$ | 162 | 0 | 162 | 3 |
| 126 | " | n-$C_8H_{17}$ | " | $C_{20}$ | 162 | 0 | 162 | 3 |
| 127 | n-$C_{12}H_{25}$ | n-$C_{12}H_{25}$ | " | $C_{20}$ | 162 | 0 | 162 | 3 |
| 128 | " | H | " | $C_{20}$ | 162 | 17 | 162 | 3 |
| 129 | " | $CH_3$ | n-$C_{12}H_{25}$ | $C_{20}$ | 162 | 159 | 162 | 3 |
| 130 | " | n-$C_8H_{17}$ | " | $C_{20}$ | 162 | 95 | 162 | 3 |
| 131 | n-$C_{14}H_{29}$ | $CH_3$ | n-$C_{14}H_{29}$ | $C_{20}$ | 166 | 159 | 166 | 3 |
| 132 | " | n-$C_8H_{17}$ | " | $C_{20}$ | 166 | 95 | 166 | 3 |
| 133 | t-octyl phenyl | $CH_3$ | t-octyl phenyl | $C_{20}$ | 145 | 159 | 145 | 3 |
| 134 | t-octyl phenyl | n-$C_8H_{17}$ | t-octyl phenyl | $C_{20}$ | 145 | 95 | 145 | 3 |
| 135 | n-$C_{16}H_{33}$ | $CH_3$ | n-$C_{16}H_{33}$ | $C_{20}$ | 139 | 159 | 139 | 3 |
| 136 | n-$C_{14}H_{29}$ | $CH_3$ | n-$C_{14}H_{29}$ | $C_{30}$ | 166 | 113 | 166 | 3 |
| 137 | n-$C_{12}H_{25}$ | $CH_3$ | n-$C_{12}H_{25}$ | $C_{30}$ | 162 | 0 | 162 | 3 |
| 138 | t-octyl phenyl | $CH_3$ | n-octyl phenyl | $C_{20}$ | 144 | 120 | 144 | 3 |
| 139 | nonylphenyl | $CH_3$ | $CH_3$,nonyl phenyl(1:1) | $C_{20}$ | 152 | 120 | 152/120 | 3 |
| 140 | " | $CH_3$ | " | $C_{30}$ | 152 | 120 | 152/120 | 3 |
| 140A | $C_{12}$-phenyl | $C_{12}$-phenyl | $C_{12}$-phenyl | $C_{20}$ | 135 | 135 | 135 | 3 |

[1]residue of "Mondur CB-75" triisocyanate
[2]residue of "Desmodur N" triisocyanate

EXAMPLES 141–153

EXAMPLE 141

Dipentaerythritol-ethylene oxide adduct capped with octadecyl isocyanate

A dipentaerythritol-ethylene oxide adduct of 18.1 hydroxyl number (3100 equivalent weight) was heated under a nitrogen sparge to remove water. Utilizing dibutyltin dilaurate as catalyst, 70 g. of the adduct was reacted with 7.06 g. of octadecyl isocyanate, providing an NCO/OH ratio of 1.06/1 equivalents. The reaction was continued at 60° C. for four days. The polymeric product was then poured into a slab mold to dry and to solidify. The structure of this product is indicated by the formula below in conjunction with Table 7, which also shows similar polymers prepared in essentially the same manner as described above, and NCO/OH proportions in equivalents.

Table 7

$$O+CH_2-C\{CH_2O-(CH_2CH_2O)_x-\underset{\underset{H}{|}}{\overset{\overset{O}{\|}}{C}}-N-R\}_3]_2$$

| Ex. No. | R | x | Equivalents NCO/OH |
|---|---|---|---|
| 141 | n-$C_{18}H_{37}$ | 70 | 1.06/1 |
| 142 | " | 27 | 0.89/1 |
| 143 | " | 44 | 0.81/1 |
| 144 | " | 44 | 0.49/1 |
| 145 | n-$C_{12}H_{25}$ | 167 | 0.9/1 |
| 146 | n-$C_{18}H_{37}$ | 167 | 0.9/1 |
| 147 | " | 27 | 0.6/1 |
| 148 | " | 70 | 0.9/1 |
| 149 | " | 70 | 0.7/1 |
| 150 | " | 70 | 0.53/1 |
| 151 | " | 44 | 1.06/1 |
| 152 | n-$C_{21}H_{25}$ | 167 | 1.25/1 |
| 153 | n-$C_{18}H_{37}$ | 167 | 1.25/1 |

EXAMPLES 154–225

Group C—Complex Polymers

As indicated above, the presence of a difunctional reactant (polyether diol or diisocyanate) in a reaction mixture with a trifunctional reactant (or higher functionality) such as a triisocyanate or trihydroxy compound, respectively, leads to complex branching in the product and a variety of polymeric products the identity of which cannot adequately be determined. However, the polymeric reaction product mixtures contain the requisite proportions of hydrophobic and hydrophilic materials for good thickening properties and therefore are useful products.

Table 8 below summarizes many of the possible combinations of reactants which provide polymeric reaction products of this class, and the proportions in equivalents of reactants effective for such reactions. The subsequent Examples and Tables illustrate these reactions more particularly.

Table 8

| | Reactant Proportions - Equivalents | | | | | | |
|---|---|---|---|---|---|---|---|
| Ex. No. | Triol | Polyether Diol | Mono-ol | Tri-NCO | Di-NCO | Mono-NCO | Mono-Amine |
| 154–180 | 1.0 | 2–5 | 1–2.5 or excess | | 75–100% of OH or excess | | |

Table 8-continued

| | | Reactant Proportions - Equivalents | | | | | |
|---|---|---|---|---|---|---|---|
| Ex. No. | Triol | Polyether Diol | Mono-ol | Tri-NCO | Di-NCO | Mono-NCO | Mono-Amine |
| 181–182 | 1.0 | 2.5 | | | 75–100% of OH and amino or excess | | 1–2.5 or excess |
| 183–189 | 1.0 | 1–3 | | | 1–3 | 75–100% of OH or excess | |
| 190–200 | | 2–7 | 1–2.5 or excess | 1.0 | 75–100% of OH or excess | | |
| 201–205 | 1.0 | | | | 0.1–0.6 | 75–100% of OH or excess | |
| 206–211 | | 1.0 | | 0.1–0.5 | | 75–100% of OH or excess | |
| 212–221 | | 0.1–1.5 | 1.5–3.0 or excess | 3.0 | | | |
| 222–225 | 0.1–1.2 | | 2.1–1.1 or excess | | 75–100% of OH or excess | | |

EXAMPLES 154–180B

EXAMPLE 154

Trimethylolpropane-PEG-TDI prepolymers capped with alcohols to provide polybranched polymers A mixture of 2.24 g. of trimethylolpropane in 150 g. of toluene and 19.56 g. of TDI were mixed at 78° C. After 15 minutes, this mixture was added to 300 g. of predried PEG (6000 molecular weight) in 300 g. of toluene containing 0.3 g. dibutyltin dilaurate. After 2 hours of 75° C., the mixture was allowed to cool to room temperature and maintained there for 72 hours. The solution was then warmed to 80° C., and split into 3 equal portions. Portion A was treated with 2.93 g. of octanol, portion B was treated with 4.27 g. of dodecanol, and portion C was treated with 6.1 g. of octadecanol. After 24 hours at 60° C., samples A, B, and C (Examples 154–156) were isolated after toluene evaporation from a slab mold.

EXAMPLE 157

Polybranched polymers from a trimethylolpropane-ethylene oxide adduct, TDI, PEG and octadecanol A mixture of 61 g. of a trimethylolpropane-ethylene oxide adduct of hydroxyl number 18.2 (3100 equivalent wt.), 240 g. of PEG (6000 molecular wt.) and 5.4 g. of octadecanol was dried by azeotropic distillation of a solution in 539 g. of toluene. The mixture was cooled to 60° C., 11.3 g. of TDI and 0.3 g. of dibutyltin dilaurate were added, and the temperature was raised to 70° C. Three hours later, 4.1 g. of octadecanol was added and the temperature was raised to 80° C. After 3 hours at 80° C., the reaction mixture was poured into a slab mold and the toluene removed by evaporation.

EXAMPLE 158

Polybranched polymer from trimethylolpropane, TDI, PEG and octadecanol

The procedure of Example 157 was followed, but 0.9 g. of TMP was substituted for the trimethylolpropane-ethylene oxide adduct of Example 157.

EXAMPLE 159

Triol-PEG adducts reacted with monohydric alcohol and diisocyanate, and capped with monohydric alcohol A mixture of 10.5 g. of "Pluracol" TP-1540 (triol adduct of propylene oxide and trimethylolpropane), 244.5 g. of PEG-6000 (eq. wt. 3700), 0.3 g. of dibutyltin dilaurate, 5.4 g. of octadecanol and 400 g. of toluene was dried by azeotropic distillation. At 60° C., 11.3 g. of tolylene diisocyanate was added. After 3 hours at 70° C., an additional 4.05 g. of octadecanol was added. After an additional 3 hours at 80° C., the mixture was poured out to air dry. Table 9 lists the foregoing and other reactants used to prepare other polymers essentially as described above. The proportion of equivalents of the reactants is given in parentheses.

In these and the subsequent Examples "TMP" is trimethylolpropane, "EO" is ethylene oxide and "PO" is propylene oxide. The subscript to EO or PO indicates the number of EO or PO units in the reactants.

Table 9

| Ex. No. | Triol (eq.) | Diol (eq.) | Mono-OH Alcohol (eq.) | Diisocyanate (Eq.) |
|---|---|---|---|---|
| 154 | TMP (1.0) | PEG-6000(2.0) | $C_8H_{17}$ (1.5) | $C_7H_6$ (4.5) |
| 155 | TMP (1.0) | PEG-6000(2.0) | $C_{12}H_{25}$ (1.5) | $C_7H_6$ (4.5) |
| 156 | TMP (1.0) | PEG-6000(2.0) | $C_{18}H_{37}$ (1.5) | $C_7H_6$ (4.5) |
| 157 | TMP . $EO_{66}$(1.0) | PEG-6000(4.0) | $C_{18}H_{37}$ (1.75) | $C_7H_6$ (6.5) |
| 158 | TMP (1.0) | PEG-6000(4.0) | $C_{18}H_{37}$ (1.75) | $C_7H_6$ (6.5) |
| 159 | TMP . $PO_8$(1.0) | PEG-7400(3.3) | $C_{18}H_{37}$ (1.75) | $C_7H_6$ (6.5) |
| 160 | TMP . $PO_8$(1.0) | PEG-7400(6.0) | $C_{18}H_{37}$ (1.0) | $C_7H_6$ (8.2) |
| 161 | TMP . $PO_8$(1.0) | PEG-7400(4.0) | $C_{18}H_{37}$ (1.0) | $C_7H_6$ (6.2) |
| 162 | TMP . $PO_3$(1.0) | PEG-7400(2.5) | $C_{18}H_{37}$ (1.5) | $C_7H_6$ (5.0) |
| 163 | TMP . $EO_{27}$(1.0) | PEG-6000(4.0) | $C_8H_{17}$ (3.75) | $C_7H_6$(7.5) |
| 164 | TMP . $EO_{27}$(1.0) | PEG-6000(4.0) | $C_{18}H_{37}$ (3.75) | $C_7H_6$ (7.5) |
| 165 | TMP . $EO_{27}$(1.0) | PEG-6000(4.0) | t-octylphenol(2.5) | $C_{13}H_{22}$ (7.5) |

Table 9-continued

| Ex. No. | Triol (eq.) | Diol (eq.) | Mono-OH Alcohol (eq.) | Diisocyanate (Eq.) |
|---|---|---|---|---|
| 166 | TMP . $EO_{27}$(1.0) | PEG-6000(4.0) | $C_{18}H_{37}$ . $EO_{125}$(2.5) | $C_{13}H_{22}$ (7.5) |
| 167 | TMP (1.0) | PEG-6000(4.0) | $C_{18}H_{37}$ . $EO_{125}$(1.5) | $C_{13}H_{22}$ (6.5) |
| 168 | TMP . $EO_{66}$(1.0) | PEG-6000(4.0) | $C_{18}H_{37}$ (1.0) | $C_{13}H_{22}$ (6.25) |
| 169 | TMP . $EO_7$(1.0) | PEG-6000(4.0) | t-octylphenol . $EO_{100}$(1.7) | $C_7H_6$ (6.5) |
| 170 | TMP . $EO_7$(1.0) | PEG-6000(4.0) | ⅔ t-octylphenol . $EO_{100}$ (1.7) ⅓ $CH_3$ . $EO_{113}$ | $C_7H_6$(6.5) |
| 171 | TMP (1.0) | PEG-6000(4.0) | ⅔ $C_{12}H_{25}$(1.5) ⅓ $CH_3$ | $C_7H_6$ (6.5) |
| 172 | TMP (1.0) | PEG-6000(5.0) | $C_{18}H_{37}$ (1.75) | $C_7H_6$ (7.5) |
| 173 | TMP (1.0) | PEG-6000(6.0) | $C_{18}H_{37}$ (0.75) | $C_7H_6$ (7.5) |
| 174 | TMP . $PO_5$(1.0) | PEG-7600(3.0) | $C_{12}H_{25}$ (1.0) | $C_7H_6$ (5) |
| 175 | TMP (1.0) | PEG-7600(7.0) | $C_{12}H_{25}$ (2.0) | $C_{13}H_{22}$ (10) |
| 176 | TMP (1.0) | PEG-7600(7.0) | $C_{10}H_{21}$ (2.0) | $C_{13}H_{22}$ (10) |
| 177 | TMP (1.0) | PEG-7600(2.5) | $C_{12}H_{25}$ (1.5) | $C_7H_6$ (5.0) |
| 178 | TMP (1.0) | PEG-7600(7.0) | $C_{14}H_{29}$ (2.0) | $C_7H_6$ (10) |
| 179 | TMP (1.0) | PEG-7600(7.0) | { $C_{12}H_{25}$ (1.7) $C_{18}H_{37}$ (0.3) } | $C_7H_6$ (10) |
| 180 | TMP (1.0) | PEG-7600(3.0) | { $C_{14}H_{29}$ (0.7) $C_{16}H_{33}$ (0.3) } | $C_7H_6$ (5.0) |
| 180A | TMP (1.0) | PEG-7600(8.0) | $C_{10}H_{21}$ (1.0) | $C_{13}H_{10}$ (10) |
| 180B | TMP (1.0) | PEG-7600(8.0) | $C_{12}H_{25}$ (1.0) | $C_{13}H_{10}$ (10) |

EXAMPLES 181–182

Polybranched Polymers from Triol, Diol, Monofunctional Amine and a Diisocyanate

EXAMPLE 181

A mixture of 2.68 g. of trimethylolpropane (60 meq.), 360 g. of PEG-6000 (120 meq., 0.36 g. of dibutyltin dilaurate and 500 g. of toluene was azeotropically distilled to remove water. Then 270 meq. (23.5 g.) of TDI was added at 50° C. After 3 hours at 75° C., one-third of the solution was removed and treated with 5.7 g. (30 meq.) of Primene 81-R, a $C_{12}$–$C_{14}$ t-alkyl primary amine. After 48 hours at 60° C. the polymeric mixture was isolated by evaporation of the toluene.

EXAMPLE 182

The procedure of Example 181 was followed using 54 g. of an ethoxylated TMP of 1200 equivalent weight (45 meq.), 540 g. of PEG-6000 (180 meq.) and 44.3 of Hylene W (337.5 meq.) diisocyanate. After 4 hours at 60° C., the sample was split into six equal fractions. To one fraction was added 5.7 g. (50 meq.) of Primene 81-R amine. After an additional 72 hours at 60° C. the polymeric mixture was isolated by evaporation of the toluene.

EXAMPLES 183–189

Polybranched polymers from PEG, a trimethylolpropane-ethylene oxide adduct, octadecyl isocyanate and a diisocyanate

EXAMPLE 183

A mixture of 225 g. of PEG (20,000 molecular weight) and 400 g. of toluene was dried by azeotropic distillation at 70° C. Then 0.225 g. of dibutyltin dilaurate and 3.34 g. of octadecyl isocyanate was added. Two hours layer, still at 70° C., 7.4 g. of "DDI" was added. In one hour, 37.5 g. of a trimethylolpropane-ethylene oxide adduct of hydroxyl number 17.1 and equivalent weight 3300 predried in toluene solution, was added. After 5 days at 60° C., the mixture was dried in a slab mold. Table 10 describes the foregoing and other reactants giving other polymeric products prepared in essentially the same manner. The proportion of equivalents of reactants is given in parentheses.

Table 10

| Ex. No. | Triol (eq.) | Diol (eq.) | Diisocyanate (eq.) | Monoisocyanate (eq.) |
|---|---|---|---|---|
| 183 | TMP . $EO_{75}$ (1.0) | PEG-20,000(2.0) | $C_{36}$ (2.0) | $C_{18}$ (1.0) |
| 184 | TMP . $EO_{73}$ (1.0) | PEG-6000 (2.0) | $C_{36}$ (2.0) | $C_{18}$ (1.0) |
| 185 | TMP . $EO_{73}$ (1.0) | PEG-6000 (2.0) | $C_{36}$ (1.5) | $C_{18}$ (0.67) |
| 186 | TMP . $EO_{117}$(1.0) | PEG-6000 (3.0) | $C_7H_6$(3.1) | $C_{18}$ (1.1) |
| 187 | TMP . $EO_{117}$(1.0) | PEG-6000 (2.0) | $C_7H_6$(2.1) | $C_{18}$ (1.1) |
| 188 | TMP . $EO_{142}$(1.0) | PEG-20,000(0.4) | $C_7H_6$ (0.9) | $C_{18}$ (0.75) |
| 189 | TMP . $EO_{142}$(1.0) | PEG-20,000(0.4) | $C_7H_6$ (0.9) | $C_{12}$ (0.75) |

EXAMPLES 190–200X

Polyethylene glycol and monohydric alcohols reacted with diisocyanate and triisocyanate

EXAMPLE 190

A mixture of 296.3 g. of PEG (molecular weight 7400 and eq. wt. 3700 by hydroxyl number), 8.1 of octadecanol, 400 g. of toluene and 0.4 g. of dibutylin dilaurate was dried by azeotropic distillation. At 60° C., 7.83 g. of tolylene diisocyanate and 5.2 g. of "Desmodur N" were added. After 3 hours at 70° C. and 3 hours at 80° C., the polymeric reaction product was poured out to air dry. Table 11 below lists the foregoing reactants and others used to prepare polymers in essentially the same manner. Equivalent proportions are given in parentheses.

Table 11

| Ex. No. | Diol (eq.) | Monol (eq.) | Triisocyanate (eq.) | Diisocyanate (eq.) |
|---|---|---|---|---|
| 190° | PEG-7400(4.0) | $C_{18}H_{37}$(1.5) | $C_{20}$(1.0) | $C_7H_6$(4.5) |
| 191 | PEG-7400(3.3) | $C_{18}H_{37}$(1.75) | $C_{30}$(1.0) | $C_7H_6$(4.5) |
| 192 | PEG-7400(4.0) | $C_{18}H_{37}$(2.0) | $C_{20}$(1.1) | $C_7H_6$(5.2) |
| 193 | PEG-7400(3.3) | $C_{18}H_{37}$(2.0) | $C_{30}$(1.1) | $C_7H_6$(4.9) |
| 194 | PEG-7400(3.3) | $C_{14}H_{29}$(1.75) | $C_{30}$(1.0) | $C_7H_6$(4.5) |
| 195 | PEG-7400(3.3) | $C_{12}H_{25}$(0.87) $C_{18}H_{37}$(0.87) | $C_{30}$(1.0) | $C_7H_6$(4.5) |
| 196 | PEG-7600(3.3) | $C_{18}H_{37}$(2.0) | $C_{30}$(1.0) | $C_7H_6$(4.4) |
| 197 | PEG-7400(2.5) | $C_{18}H_{37}$(1.5) | $C_{30}$(1.0) | $C_7H_6$(3.25) |
| 198 | PEG-7400(4.0) | $C_{18}H_{37}$(2.0) | $C_{30}$(0.84) | $C_7H_6$(5.1) |
| 199 | PEG-7400(7.0) | $C_{12}H_{25}$(2.0) | $C_{30}$(1.0) | $C_7H_6$(8.0) |
| 200 | PEG-7400(4.0) | $C_{12}H_{25}$(0.7) $C_{18}H_{37}$(0.3) | $C_{30}$(1.0) | $C_7H_6$(4.0) |
| 200A | PEG-7600(9.0) | $C_{20}H_{41}$(1.0) | $C_{30}$(1.0) | $C_7H_6$(9.0) |
| 200B | " | " | " | $C_{13}H_{22}$(9.0) |
| 200C | " | $C_{14}H_{29}$(1.0) | " | $C_{13}H_{10}$(9.0) |
| 200D | " | $C_{16}H_{33}$(1.0) | " | " |
| 200E | " | $C_{18}H_{37}$(1.0) | " | " |
| 200F | " | $C_{20}H_{41}$(1.0) | " | " |
| 200G | PEG-7600(9.5) | $C_{18}H_{37}$(0.5) | " | " |
| 200H | PEG-7600(8.5) | $C_{18}H_{37}$(1.5) | " | " |
| 200I | PEG-7600(8.0) | $C_{18}H_{37}$(2.0) | " | " |
| 200J | PEG-7600(9.5) | $C_{20}H_{41}$(0.5) | " | " |
| 200K | PEG-7600(8.5) | $C_{20}H_{41}$(1.5) | " | " |
| 200L | PEG-7600(8.0) | $C_{20}H_{41}$(2.0) | " | " |
| 200M | PEG-7600(9.0) | $C_{18}H_{37}$(1.0) | PAPI 901(5.0) | $C_7H_6$(5.0) |
| 200N | " | " | PAPI 901(3.0) | $C_7H_6$(7.0) |
| 200O | " | $C_{10}H_{21}$(1.0) | PAPI 901(5.0) | $C_7H_6$(5.0) |
| 200P | " | $C_{12}H_{25}$(1.0) | PAPI 901(5.0) | " |
| 200Q | " | " | PAPI 901(3.0) | $C_7H_6$(7.0) |
| 200R | " | $C_{18}H_{37}$(1.0) | PAPI 135(1.0) | $C_7H_6$(9.0) |
| 200S | " | " | PAPI 135(2.0) | $C_7H_6$(8.0) |
| 200T | " | $C_{12}H_{25}$(1.0) | " | " |
| 200U | " | $C_{12}H_{25}$(1.0) | PAPI 901(4.0) | $C_7H_6$(6.0) |
| 200V | " | $C_{14}H_{29}$(1.0) | PAPI 901(3.0) | $C_7H_6$(7.0) |
| 200W | " | $C_{10}H_{21}$(1.0) | PAPI 901(4.0) | $C_{13}H_{10}$(6.0) |
| 200X | " | $C_{12}H_{25}$(1.0) | PAPI 901(3.0) | $C_{13}H_{10}$(7.0) |

EXAMPLES 201–205

Trimethylolpropane-ethylene oxide adduct reacted with octadecyl isocyanate and diisocyanate

EXAMPLE 201

A mixture of 150 g. of a trimethylolpropane-ethylene oxide adduct of 9.7 hydroxyl number (eq. wt. 5800) and 200 g. of toluene was dried by azeotropic distillation. Then, 0.15 g. of dibutyltin dilaurate, 6.11 g. of octadecyl isocyanate and 3.09 of "DDI" was added at 60° C. After 5 days at 60° C., the polymeric product was isolated after the toluene evaporated from a slab mold. Table 12 below describes the foregoing and other reactants used to prepare polymers essentially as described with respect to Example 201. Reactant proportions in equivalents are given in parentheses.

Table 12

| Ex. No. | Triol (eq.) | Diisocyanate (eq.) | Monoisocyanate (eq.) |
|---|---|---|---|
| 201 | TMP . $EO_{132}$ (1.0) | $C_{36}$ (0.4) | $C_{18}$ (0.8) |
| 202 | TMP . $EO_{132}$ (1.0) | $C_{36}$ (0.4) | $C_{12}$ (0.8) |
| 203 | TMP . $EO_{142}$ (1.0) | $C_{36}$ (0.4) | $C_8$ (0.8) |
| 204 | TMP . $EO_{116}$ (1.0) | $C_{36}$ (0.4) | t-$C_{12}$ (0.8) |
| 205 | TMP . $EO_{116}$ (1.0) | $C_{36}$ (0.4) | t-$C_{18}$ (0.8) |

EXAMPLES 206–211

Mono isocyanate capped polymers from triisocyanate

EXAMPLE 206

A mixture of 150 g. of polyoxyethylene glycol (6000 molecular weight), 150 g. toluene and dibutyltin dilaurate catalyst was dried by azeotropic distillation. At 70° C., 5.93 g. of dodecyl isocyanate was added. After 2 hours at 70° C. isocyanate consumption was complete, and 4.49 g. of 75% Desmodur-N triisocyanate was added. The reaction mixture was held at 60° C. for 18 hours and then dried in a slab mold. Table 13 below lists the foregoing and other reactants used to prepare polymers in essentially the same manner. Proportions in equivalents are given in parentheses.

TABLE 13

| Ex. No. | Diol (eq.) | Triisocyanate (eq.) | MonoHCO (eq.) |
|---|---|---|---|
| 206 | PEG-6000 (1.0) | $C_{20}$ (0.4) | $C_{18}$ (0.7) |
| 207 | PEG-20,000(1.0) | $C_{20}$ (0.4) | $C_{18}$ (0.7) |
| 208 | PEG-6000 (1.0) | $C_{20}$ (0.4) | $C_{12}$ (0.7) |
| 209 | PEG-20,000(1.0) | $C_{20}$ (0.4) | $C_{12}$ (0.7) |
| 210 | PEG-6000 (1.0) | $C_{20}$ (0.4) | $C_{12}$ (0.35) $C_{18}$ (0.35) |
| 211 | PEG-20,000(1.0) | $C_{20}$ (0.4) | $C_{12}$ (0.35) $C_{18}$ (0.35) |

EXAMPLES 212-221

Alcohol capped polymers from triisocyanates

EXAMPLES 212 and 213

A mixture of 70 g. of a dodecyl alcohol-ethylene oxide adduct (4800 molecular weight) and 90 g. of toluene was azeotropically distilled with water evolution ceased. Then, at 60° C., 0.07 g. of dibutyltin dilaurate and 6.01 g. of Desmodur-N triisocyanate were added. After 80 minutes at 60° C., an infrared spectrum indicated complete consumption of hydroxyl. To 85 g. of the resulting reaction mixture was added 27 g. of a 50% PEG (6000 molecular weight) solution in toluene (A); to 45 g. of the reaction mixture was added 59 g. 40% PEG (20,000 molecular weight) in toluene (B). After an additional 3 hours at 60° C., polymer samples A and B (Examples 212, 213) were poured out to air dry. Table 14 below lists the foregoing and other reactants used to prepare products essentially as described above. Proportions in equivalents are given in parentheses.

Table 14

| Ex. No. | Diol (eq.) | Triisocyanate (eq.) | Monol (eq.) |
|---|---|---|---|
| 212 | PEG-6000 (1) | $C_{20}$ (3) | $C_{12} \cdot EO_{105}$ (2) |
| 213 | PEG-20,000 (1) | $C_{20}$ (3) | $C_{12} \cdot EO_{105}$ (2) |
| 214 | PEG-20,000 (1) | $C_{20}$ (3) | $C_{13} \cdot EO_{114}$ (2) |
| 215 | PEG-6000 (1) | $C_{20}$ (3) | $C_{16} \cdot EO_{139}$ (2) |
| 216 | PEG-20,000 (1) | $C_{20}$ (3) | $C_{16} \cdot EO_{159}$ (2) |
| 217 | PEG-6000 (1) | $C_{20}$ (3) | $C_{18} \cdot CO_{150}$ (2) |
| 218 | PEG-20,000 (1) | $C_{20}$ (3) | $C_{18} \cdot CO_{150}$ (2) |
| 219 | PEG-6000 (1) | $C_{20}$ (3) | t-octylphenyl . $EO_{145}$ (2) |
| 220 | PEG-20,000 (1) | $C_{20}$ (3) | t-octylphenyl . $EO_{145}$ (2) |
| 221 | PEG-6000 (1) | $C_{20}$ (3) | $C_{14} \cdot EO_{114}$ (2) |

EXAMPLES 222-225

Polybranched polymers from triol, monol and diisocyanate

Essentially as described in Examples 154-158, polymeric reaction products were prepared from the reactants and in the proportions (by equivalents) listed in Table 15 below.

Table 15

| Ex. No. | Triol (eq.) | Monol (eq.) | Diisocyanate (eq.) |
|---|---|---|---|
| 222 | TMP . $EO_{157}$ (1.0) | $C_{18}H_{37} \cdot EO_{211}$(1.25) | $C_7H_6$ (2.3) |
| 223 | TMP . $EO_{157}$ (1.0) | $C_{12}H_{25} \cdot EO_{137}$(1.25) | $C_7H_6$ (2.3) |
| 224 | TMP . $EO_{157}$ (1.0) | $C_{14}H_{29} \cdot EO_{168}$(1.25) | $C_7H_6$ (2.3) |
| 225 | TMP . $EO_{157}$ (1.0) | $C_{16}H_{33} \cdot EO_{107}$(1.25) | $C_7H_6$ (2.3) |

EXAMPLES 226-235

A. Preparation of water solutions of thickeners

Table 16 below shows Brookfield viscosity measurements on 3% water solutions of various polymeric thickeners identified under previous Examples of this specification. The solutions were prepared by standard mixing techniques.

B. Preparation of polymer emulsions

Table 16 below also reports Brookfield and ICI viscosities of various polymer emulsions prepared by standard mixing techniques from the following recipe, wherein the thickeners are further identified above under polymer Examples:

|  | parts by weight |
|---|---|
| Acrylic copolymer (46.5% solids)[1] | 80.0 |
| Water | 11.2 |
| Water solution of thickness,[2] 3% | 24.8 |

C. Preparation of latex paint compositions

Table 16 below also indicates properties of paint compositions containing polymeric thickeners of the foregoing Examples, or hydroxyethylcellulose (HEC). The recipe for the paint compositions follows. The pigment grind, premix and thickener solutions are prepared separately and the intermixed with the other ingredients in the order given. Mixing techniques and equipment are conventional. The thickener solutions contain 3.2% by weight of HEC or 6% by weight of a thickener of the invention and the final paints are formulated to contain 1% by weight of thickener based on emulsion polymer solids.

| Pigment Grind Portion: | Parts by Weight |
|---|---|
| Dispersant (Tamol 731) | 10.8 |
| Defoamer (Nopco NDW) | 2.0 |
| $TiO_2$ (Ti Pure R-900) | 296.0 |
| Let-down Portion: | |
| Propylene glycol | 57.8 |
| Polymer emulsion[1] A or B | 557.9 |
| Pre-mix: | |
| Preservative (Super Ad-It) | 1.0 |
| Water | 15.2 |
| Coalescent (Texanol) | 15.7 |
| Anionic surfactant (Triton CR-7) | 2.0 |
| Defoamer (Nopco NDW) | 2.9 |
| Thickener Solution: | 80.4 |

Table 16 shows that efficient thickening of latex paints and simple polymer emulsions is not predictable on the basis of water thickening alone, even though HEC thickens water effectively. The Table also shows that in many cases the polymeric thickeners of the invention thicken latex paints with the same or greater efficiency (viscosity improvement relative to amount of thickener) than does HEC, and that best overall performance in latex paints (thickening, flow and leveling, film build in terms of high ICI viscosity is obtained from polyurethanes having a multiplicity of hydrophobic groups—Examples 226 and 229.

Table 16

| Paint Ex. No. | Polymer Ex. No. | Polymer[1] Emulsion | Brookfield (cps) Water Solution | Brookfield (cps) Emulsion[2] | Brookfield (cps) Paint | Stormer ($KU^3$) Initial | Stormer ($KU^3$) Hand Stirred | Stormer ($KU^3$) Sheared | $ICI^4$ (poise) Emulsion | $ICI^4$ (poise) Paint | Gloss[5] 60° Exp. | Gloss[5] 60° HEC | Flow[6] and Leveling |
|---|---|---|---|---|---|---|---|---|---|---|---|---|---|
| 226 | 1 | A | 22000 | 80 | 734 | 64 | 68 | 68 | 0.38 | 0.91 | 72 | 70 | 5 |
|  |  | B |  | 140 | 1060 | 74 | 79 | 78 | 0.80 | 0.91 | 73 | 68 | 6 |
| 227 | 2 | A | <20 | 57 | 960 | 63 | 68 | 63 | 0.28 | 0.79 | 67 | 71 | 5 |
|  |  | B |  | 92 | 2190 | 81 | 86 | 85 | 0.50 | 0.72 | 70 | 64 | 2 |
| 228 | 3 | A | 20 | 350 | 1220 | 71 | 74 | 70 | 0.31 | 0.70 | 50 | 71 | 4 |
|  |  | B |  | 12100 | 6040 | 135 | 137 | 136 | 0.42 | 0.48 | 69 | 65 | 1 |
| 229 | 17A | A | 39400 | 26600 | 6390 | 114 | 113 | 113 | 0.52 | 0.90 | 65 | 67 | 3 |

Table 16-continued

| Paint Ex. No. | Polymer Ex. No. | Polymer[1] Emulsion | Viscosity Brookfield (cps) Water Solution | Emulsion[2] | Paint | Stormer (KU[3]) Initial | Hand Stirred | Sheared | ICI[4] (poise) Emulsion | Paint | Gloss[5] 60° Exp. | HEC | Flow[6] and Leveling |
|---|---|---|---|---|---|---|---|---|---|---|---|---|---|
| | | B | | 42500 | 17100 | >141 | >141 | >141 | 1.08 | 0.65 | 69 | 66 | 3 |
| 230 | 20 | A | <20 | 57 | 860 | 63 | 68 | 63 | 0.28 | 0.89 | 71 | 71 | 5 |
| | | B | | 13 | 2770 | 86 | 92 | 89 | 0.55 | 0.94 | 72 | 67 | 1 |
| 231 | 21 | A | 600 | 500 | 2390 | 88 | 93 | 90 | 0.42 | 0.91 | 72 | 69 | 3 |
| | | B | | 5040 | 8480 | 127 | 137 | 136 | 1.15 | 0.76 | 74 | 66 | 2 |
| 232 | 23 | A | <20 | 69 | 800 | 63 | 67 | 65 | 0.30 | 0.89 | 73 | 73 | 7, sag |
| | | B | | 59 | 2000 | 75 | 82 | 76 | 0.58 | 0.93 | 71 | 66 | 2 |
| 233 | 24 | A | 495 | 750 | 2320 | 88 | 93 | 90 | 0.57 | 0.91 | 72 | 69 | 4 |
| | | B | | 2930 | 6840 | 121 | 132 | 124 | 1.20 | 0.84 | 72 | 64 | 2 |
| 234 | 154 | A | <20 | 76 | 1150 | 69 | 72 | 61 | 0.33 | 0.89 | 73 | 72 | 4 |
| | | B | | 291 | 4190 | 95 | 98 | 94 | 0.70 | 0.95 | 72 | 67 | 1 |
| 235 | 155 | A | 435 | 660 | 2590 | 90 | 93 | 88 | 0.56 | 0.75 | 70 | 66 | 4 |
| | | B | | 3070 | 13200 | 135 | 138 | 137 | 1.26 | 0.68 | 74 | 67 | 0 |

[1]Polymer Emulsion A is Rhoplex AC-490 copolymer acrylic emulsion (46.5% solids); Polymer Emulsion B is Rhoplex AC-61 copolymer acrylic emulsion (46.5% solids).
[2]Thickener solids on emulsion polymer solids is 2%.
[3]Krebs units - low shear viscosity.
[4]High shear viscosity as measured on the ICI Cone and Plate Viscosimeter (Research Equipment Limited, London) operating at about 10,000 sec.$^{-1}$ shear rate to simulate the shear applied to a paint during brushing. Generally, as ICI viscosity increases, film thickness ("build") also increases. Good build translates to increased hiding power of the paint and also contributes to improved flow and leveling.
[5]Determined by comparing side-by-side drawdowns of control paint (containing HEC as thickener) and the experimental paint ("Exp.") containing a thickener of the invention, on a Leneta Form 1B "Penopac" chart. The gloss measurements were made instrumentally.
[6]Visual examination of brushmarks on a Leneta Form 12H Spreading Rate chart. Ratings are on a 0-10 scale where 10 is exceptionally superior flow and leveling and 0 represents totally unacceptable flow and leveling.

EXAMPLES 236-238

Table 17 below compares properties of latex paint compositions containing a thickener of the invention or hydroxyethylcellulose (HEC). The formulations of Examples 236 and 237 are the same as in the paint Examples of Table 16 but the paint formulation of Example 238 is as follows (prepared by standard mixing in the order given) wherein the amount of thickener is 2% based on emulsion polymer solids:

| Pigment Grind Portion: | Parts by Weight |
|---|---|
| Water | 85.0 |
| Dispersant (Tamol 731) | 8.0 |
| Dispersant (tetrasodium pyrophosphate) | 0.3 |
| Surfactant (Tergitol NPX) | 2.0 |
| Mildeweide (Super-Ad It) | 1.0 |
| Ethylene glycol | 20.0 |
| Coalescent (hexylene glycol) | 15.0 |
| 2-Ethylhexyl acetate | 5.0 |
| Defoamer (Nopco NDW) | 2.5 |
| TiO$_2$-rutile (Ti Pure R-901) | 175.0 |
| TiO$_2$-anatase (Titanox 1000) | 50.0 |

| Pigment Grind Portion: | Parts by Weight |
|---|---|
| Mica, water-ground (325 mesh) | 25.0 |
| Talc (Nytol 300) | 125.0 |
| Let-down Portion: | |
| Water | 36.1 |
| Polymer emulsion | 400.0 |
| Defoamer (Nopco NDW) | 2.5 |
| Thickener solution | 170.9 |

Table 17 illustrates preferred thickeners of the invention with respect to utility in latex paint compositions since excellent balance between thickening efficiency, flow and leveling is demonstrated as compared with paints containing hydroxyethylcellulose.

Table 17

| Ex. No. | Polymer Ex. No. | Polymer Emulsion | Viscosity Stormer (KU) Initial | Hand Stirred | Sheared | ICI (poise) Paint | Flow/Leveling (10 best) | Gloss 60° |
|---|---|---|---|---|---|---|---|---|
| 236 | 44 | Rhoplex AC-61 acrylic | 107 | 118 | 113 | 1.00 | 9 | |
| | HEC | Rhoplex AC-61 acrylic | 76 | 84 | 79 | 0.59 | 2 | |
| 237 | 74A | Rhoplex AC-490 acrylic | 93 | 98 | 95 | 1.01 | 5 | 80 |
| | HEC | Rhoplex A-490 acrylic | 86 | 100 | 83 | 1.15 | 4 | 79 |
| 238 | 199 | UCAR 360 vinyl-acrylic | 107 | 114 | 107 | 1.85 | 8 | |
| | HEC | UCAR 360 vinyl-acrylic | 98 | 104 | 98 | 1.19 | 4 | |

EXAMPLE 239

A 600 g. sample of polyethylene glycol of 20,000 nominal molecular weight was dried by azeotropic distillation of a toluene (200 g.) solution thereof. At 60° C., 0.6 g. of dibutyltin dilaurate and 21.6 g. of octadecyl isocyanate was added. After a further 72 hours at 60° C.

the mixture was poured into a slab mold to allow the toluene to evaporate and to isolate the solid polymer. The product has the structure $C_{18}H_{37}NHCO-O(CH_2CH_2O)_{455}-CONHC_{18}H_{37}$ and is representative of polymeric thickeners of U.S. Pat. No. 3,770,684—Singer et al.

EXAMPLE 240

The procedure of Example 226 was repeated in all essential respects but using polyethylene glycol of 6000 molecular weight and dodecyl isocyanate inplace of octadecyl isocyanate. The product has the structure $C_{12}H_{25}NHCO-O(CH_2CH_2O)_x-OCONHC_{12}H_{25}$ and is a lower molecular weight version of the polymeric thickeners of U.S. Pat. No. 3,770,684.

EXAMPLES 241-245

A series of polymers were prepared having the general structure $A-E+B-E)_{\overline{n}}A$ where A is the residue of an aliphatic monohydroxy alcohol, E is the polyether residue of a polyethylene glycol having about 100-200 ethylene oxide units, n is 1, and B is a urethane radical, that is, the residue of an organic diisocyanate resulting from reaction of the isocyanate groups with the terminal hydroxyl groups of the polyoxyethylene glycol. These polymers are further described in terms of reactants as follows, where "TDI" is tolylene diisocyanate, "Hylene W" is 4,4'-methylene-bis(isocyanatocyclohexane) and "$C_{12}OH$" or "$C_{18}OH$" refers to dodecyl or octadecyl alcohol:

Table 18

| | | Molecular Wt. of E | | |
|---|---|---|---|---|
| Example | Diisocyanate/alcohol | Wt. Avg. | No. Avg. | EtO units |
| 241 | TDI/$C_{12}$OH | 14850 | 9390 | 208 |
| 242 | TDI/$C_{12}$OH | 9620 | 6500 | 159 |
| 243 | TDI/$C_{12}$OH | 6250 | 5010 | 105 |
| 244 | Hylene W/$C_{12}$OH | 9620 | 6500 | 159 |
| 245 | TDI/$C_{18}$OH | 16550 | 10400 | 215 |

The polymers of Examples 241-245 are representative of the polymeric thickeners in the oil-in-water pigment printing paste emulsions of German Pat. No. 2,054,885 filed Nov. 7, 1970.

Table 19 below summarizes the structures of the polymers of Examples 239-245 and structures of polymers of previous examples for convenience in relating structure of the thickeners to their effectiveness in the latex paint compositions of Table 20.

Table 19

| Polymer Ex. No. | Structure | Eq. Weight Ratios |
|---|---|---|
| 239 | (EO)$_{455}$/C$_{18}$-NCO | 1.0/1.0 |
| 240 | (EO)$_{455}$/C$_{12}$-NCO | 1.0/1.0 |
| 241 | C$_{12}$O(EO)$_{208}$$^{mm}$H/TDI | 1.0/1.0 |
| 242 | C$_{12}$O(EO)$_{159}$H/TDI | 1.0/1.0 |
| 243 | C$_{12}$O(EO)$_{105}$H/TDI | 1.0/1.0 |
| 244 | C$_{12}$O(EO)$_{159}$$^{mm}$H/Hy . W | 1.0/1.0 |
| 245 | C$_{18}$O(EO)$_{215}$H/TDI | 1.0/1.0 |
| 47 | C$_{12}$OH/E-6000/TDI | 0.05/0.95/1.0 |
| 50 | " | 0.10/0.90/1.0 |
| 44 | " | 0.20/0.80/1.0 |
| 38 | " | 0.30/0.70/1.0 |
| 61 | " | 0.40/0.60/1.0 |
| 58 | " | 0.50/0.50/1.0 |
| 54 | C$_{10}$OH/E-6000/TDI | 0.20/0.80/1.0 |
| 51 | C$_8$OH/E-6000/Hy . W | " |
| 63 | Pr . 81R/E-6000/TDI | " |
| 74B | Menthol/E-6000/Hy . W | " |
| 74C | DCPA/E-6000/TDI | 0.30/0.70/1.0 |
| 96A | C$_{12}$(EO)/E-6000/TDI | 0.30/0.70/1.0 |
| 96B | C$_{12}$(EO)/E-6000/TDI | " |

Table 19-continued

| Polymer Ex. No. | Structure | Eq. Weight Ratios |
|---|---|---|
| 1 | DDI/E-6000/TDI | 0.40/1.0/0.80 |
| 11 | ODI/E-6000/TDI | 0.50/1.0/1.50 |
| 178 | C$_{14}$OH/TMP/E-6000/TDI | 0.1/0.1/0.8/1.0 |
| 135 | C$_{16}$(EO)/C$_1$(EO)/Des . N | 0.7/0.3/1.0 |

EXAMPLES 246-269

Table 20 below compares properties of latex paint compositions containing as thickener a polymer of Examples 239 and 240, less preferred polymers of the present invention (Examples 241-245), preferred polymers of this invention (remaining polymer examples), or hydroxyethyl cellulose (HEC). The HEC of all examples is "NATROSOL 250 MR", a product of Hercules, Inc. The paint formulations and test procedures were essentially the same as repoted in Table 16, including polymer emulsions A and B.

The Table shows the overall superiority afforded by polymeric thickeners of the invention, and especially, the excellent control of paint rheology that may be achieved by systematic variation of thickener structure. Thus, the prior art latex paints of Example 246 and the latex paints of Example 247 exhibits much poorer flow than do the majority of the preferred paints of the present invention (Examples 253-269), at comparable or even lower viscosity. Hydroxyethyl cellulose also confers very poor flow.

Examples 248-252 contain thickeners based on the German Pat. No. 2,054,885. For Emulsion A, these thickeners are clearly less efficient; in fact, at twice the level, these thickeners (except for Example 252) do not even generate the Stormer viscosity generally demanded for good paint transfer without severe dripping (72-80 KU). These thickeners, like HEC, are also relatively inefficient with respect to the development of brushing viscosity (ICI) in the paints based on Emulsion B.

Thus, the paint rheological properties achievable with the thickeners of the present invention may be made to range from the exceptionally efficient in terms of Stormer viscosity with markedly improved flow and acceptable brushing viscosity (Examples 267-269) to the relatively inefficient but with superb flow and brushing viscosity (Examples 261A and 261B). Materials of the latter characteristics are highly desirable in some instances. For example, such a material may be added to the latex either prior to manufacture of the paint or at any intermediate stage of paint manufacture without introducing problems of excessive viscosity in handling and processing. Stormer viscosity can then be later adjusted to any desired level with efficient types of thickeners, either those known in the art (such as HEC) or of the present invention such as those of Examples 267-269.

Within the noted extremes of performance characteristics, one can also achieve a superior balance of high Stormer viscosity efficiency, high brushing viscosity, and excellent flow. Exemplary materials include those of Examples 253-255, 259, 260, and to a lesser degree depending on the polymer used, the remaining novel thickeners of Table 20. For example, the thickeners of Examples 262 and 263 provide good overall performance in Emulsion B but flow is compromised in Emulsion A.

Paints containing thickeners of the invention also exhibit good shelf stabilities in tests comparing hand-stirred and sheared Stormer viscosity, and ICI viscosity, of samples stored at 72° F. (50% relative humidity) or subjected to heating at 140° F. or freeze-thawing.

Table 20

| | | Latex Paint Properties | | | | | | | |
|---|---|---|---|---|---|---|---|---|---|
| | | Polymer Emulsion A | | | | Polymer Emulsion B | | | |
| Paint Ex. No. | Polymer Ex. No. | % Thickener on emulsion solids | Stormer Viscosity (KU) | ICI Viscosity (poise) | Flow/ Leveling (10 best) | % Thickener on emulsion solids | Stormer Viscosity (KU) | ICI Viscosity (poise) | Flow/ Leveling (10 best) |
| 246 | 239 | 0.65 | 86 | 0.80 | 3 | 0.2 | 82 | 0.30 | 6 |
| 247 | 240 | 1.0 | 71 | 1.00 | 3 | 1.0 | 95 | 1.00 | 0 |
| 248 | 241 | 2.0 | 67 | 1.02 | 9 | 2.0 | 80 | 1.00 | 9 |
| 249A | 242 | 2.0 | 67 | 1.05 | 8 | 2.0 | 90 | 1.10 | 5 |
| 249B | 242 | 1.0 | 67 | 0.82 | 5 | 1.0 | 72 | 0.52 | 4 |
| 250 | 243 | 2.0 | 69 | 1.04 | 5 | 2.0 | 109 | 0.98 | 0 |
| 251A | 244 | 2.0 | 64 | 0.91 | 9 | 2.0 | 75 | 0.89 | 9 |
| 251B | 244 | 1.0 | 64 | 0.79 | 10 | 1.0 | 63 | 0.49 | 7 |
| 252A | 245 | 2.0 | 86 | 0.93 | 9 | 2.0 | 118 | 0.61 | 5 |
| 252B | 245 | | | | | 1.0 | 100 | 0.44 | 6 |
| 253 | 47 | 1.0 | 73 | 1.20 | 9 | | | | |
| 254 | 50 | 1.0 | 82 | 1.15 | 8 | | | | |
| 255 | 44 | 1.0 | 93 | 1.20 | 6 | 1.0 | 106 | 0.92 | 9 |
| 256 | 38 | 1.0 | 90 | 1.10 | 2 | | | | |
| 257 | 61 | 1.0 | 96 | 1.07 | 2 | | | | |
| 258 | 58 | 1.0 | 97 | 1.03 | 0 | | | | |
| 259 | 54 | 1.0 | 77 | 1.15 | 8 | 1.0 | 84 | 0.94 | 8 |
| 260 | 51 | 1.0 | 80 | 1.10 | 7 | 1.0 | 92 | 0.81 | 9 |
| 261A | 63 | 1.0 | 71 | 1.02 | 9 | 1.0 | 67 | 0.79 | 10 |
| 261B | 63 | 2.0 | | | | 2.0 | 67 | 1.01 | 10 |
| 262 | 74B | 1.0 | 91 | 1.11 | 4 | 1.0 | 93 | 0.93 | 8 |
| 263 | 74C | 1.0 | 89 | 1.30 | 3 | 1.0 | 95 | 1.39 | 6 |
| 264 | 96A | 1.0 | 70 | 1.01 | 8 | 1.0 | 64 | 0.80 | 10 |
| 265 | 96B | 1.0 | 71 | 1.02 | 6 | 1.0 | 73 | 0.87 | 9 |
| 266 | 1 | 1.0 | 67 | 0.88 | 8 | 1.0 | 77 | 0.87 | 9 |
| 267A | 11 | 1.0 | 102 | 0.92 | 6 | 1.0 | 138 | 0.62 | 7 |
| 267B | 11 | 0.5 | | | | 0.5 | 111 | 0.51 | 7 |
| 268 | 178 | 1.0 | 118 | 1.01 | 4 | 0.5 | 116 | 0.61 | 7 |
| 269 | 135 | 1.0 | 86 | 0.75 | 6 | 1.0 | 136 | 0.50 | 4 |
| | HEC | 1.0 | 83 | 1.21 | 3–4 | 1.0 | 76 | 0.62 | 2–3 |
| | CONTROL | 0.0 | 65 | 0.60 | 10 | 0.0 | 55 | 0.40 | 10 |

EXAMPLE 270

Pigment Printing Paste

A pigment printing paste conventionally consists of three major ingredients: pigment, thickener, and binder. Before these ingredients are mixed to form a print paste, a "cut clear" is formed with a thickener and a color concentrate. Typically, the cut clear is prepared by dissolving in water 6% by weight of a thickener, such as the polymeric thickener of Example 158, and admixing for about 30 minutes to form a translucent gel of consistency over 100,000 cps. The cut clear functions as a viscosity builder in the paste.

Next, the color concentrate is prepared, for example by blending over about 15 minutes 45.2% of a presscake dispersion (a pigment dispersion in water), 18% of the cut clear, and 36.8% of water until a flowing creamy paste of about 1900 cps viscosity results.

The print paste is formed by mixing 10% of the color concentrate and 10% of an emulsion binder (of about 40–50% solids). A suitable binder is Rhoplex E-32 acrylic polymer emulsion, 46.0% solids. The resultant composition is a paste of 28,000 cps viscosity and is ready for printing use on cotton, polyester, cotton-polyester fabric blends and the like.

If desired the pigment printing pastes may be formulated as oil-in-water emulsions by the addition of a water immiscible organic solvent such as toluene, in the manner of German Pat. No. 2,054,885. The printing pastes may also contain dispersing aids, such as any of the well-known ionic or nonionic surfactants, and auxiliary thickeners such as a "Carbopol" carboxy vinyl polymer.

EXAMPLE 271

Acid Dye Print Paste

A typical acid dye print paste formulation utilizing polymeric products of the invention is the following:

| | Wt. % |
|---|---|
| Dye solution - Acid Blue-25, 6% | 12.5 |
| Cut clear (6%) of Example 270 | 25.0 |
| Formic Acid | 1.8 |
| Nopco "Foam Master" DF-160L Anti-foaming agent | .2 |
| Water | 60.5 |

The ingredients are admixed for about 15 minutes in a smooth, creamy paste of pH 2.0–2.3 and a viscosity of about 1600 cps. The paste may be applied to a fabric such as carpeting by conventional techniques, such as by use of a Zimmer flat bed screen.

EXAMPLE 272

Textile Coating Formulation

The polymeric thickeners of this invention are effective for the thickening of various textile polymer coatings. A typical formulation useful as a flocking adhesive is the following:

| | |
|---|---|
| Rhoplex HA-8 acrylic polymer (46% solids) | 300.0 |

-continued

| | parts by weight |
|---|---|
| Catalyst solution NH4NO3 (25% solids) | 60.0 |
| Cut clear (6%) of Example 270 | 30.0 |

The formulation has a creamy consistency of about 40,500 cps and may be applied to a textile fabric in a conventional manner, such as by padding, dipping, roller coating or other coating or impregnating techniques.

EXAMPLE 273

Pigmented Paper Coatings

The polymeric thickeners of the invention are useful in pigmented paper coatings in place of natural products such as sodium alginate and carboxymethyl cellulose. A typical formulation follows.

In a suitable container 72.6% by weight of clay (70% solids), 18.3% of Dow-620 carboxylated styrene-butadiene polymer emulsion as a pigment binder (50% solids), 1% of the cut clear of Example 270 and 8.1% water are mixed. This formulation when pigmented may be applied to paper by a trailing blade in a known manner. It has a consistency of about 1800 cps.

EXAMPLE 274

Cleaner and Rust Remover

The increased viscosity due to the thickener in the following formulation permits easy application of the cleaner to vertical surfaces such as aircraft and truck bodies, as an aluminum and stainless steel cleaner and brightener.

| | |
|---|---|
| Phosphoric Acid (85%) | 47.2 parts by weight |
| Butyl Cellosolve | 16.0 |
| Triton X-100 nonionic surfactant | 2.0 |
| Polymeric Thickener of Example 191 | 3.0 |
| Water | 30.8 |

EXAMPLE 275

Herbicidal Formulation

To prevent drift and to keep post-emergence herbicide in contact with leafy surfaces, a thickener may be added to a spray tank mix formulation as follows:

| | |
|---|---|
| 2,4-D diethanolamine salt (herbicide) | 5.0 lbs. |
| Polymeric Thickener of Example 164 | 4.0 lbs. |
| Sodium lauryl sulfate (27%) | 2.5 lbs. |
| Water to make 100 gallons | |

EXAMPLE 276

Herbicide Spray Mix

The following spray mix formulation has a viscosity of 200 centipoise and exhibits an increase in spray retention and decrease in misting as compared to solutions without thickener.

| | |
|---|---|
| Sodium Trichloroacetate | 8 lbs. |
| Polymeric Thickener of Example 168 | 4 lbs. |
| Triton X-102 nonionic surfactant | 3 lbs. |
| Water to make 100 gallons | |

EXAMPLE 277

Aqueous gels such as those of U.S. Pat. No. 3,740,421 can be formulated with only 3 to 10% of the polymeric thickeners of the invention as compared with 20–90% of the polyoxyethylated polyoxypropylene glycols of the patent. In a typical formulation, 4 grams of the polymeric thickener of Example 164 is admixed by constant stirring into 96 g. of water. When the thickener has dissolved, a translucent ringing gel results.

EXAMPLE 278

Topical Medicinal

The following formulation is a soft, translucent gel useful as a topical bactericide and fungicide:

| | Parts by wt. |
|---|---|
| Polymeric Thickener of Example 191 | 4.0 |
| Boric Acid | 4.76 |
| Water | 91.24 |
| | 100 |

EXAMPLE 279

Topical Medicinal

The following formulation is a soft opaque gel for external medicinal use:

| | Parts by wt. |
|---|---|
| Polymeric Thickener of Example 164 | 4.0 |
| Zinc Oxide | 8.6 |
| Water | 87.4 |
| | 100 |

EXAMPLE 280

Cosmetic

A moisturizing cream is formulated as follows:

| | Parts by wt. |
|---|---|
| Cetyl alcohol | 2.0 |
| Mineral Oil | 5.0 |
| Glycerol monooleate | 6.0 |
| Methyl paraben | 0.1 |
| Propylene glycol | 5.0 |
| Polymeric Thickener of Example 157 | 2.5 |
| Deionized water | 79.4 |
| | 100 |

EXAMPLE 281

A useful protein hair conditioner and texturizer formula is as follows:

| | Parts by wt. |
|---|---|
| Polypeptides solution (Stepan Chemical) | 5.0 |
| Polymeric thickener of Example 191 | 1.5 |
| Methyl Paraben | 0.1 |
| Arquad 2 HT-75 Conditioner | 0.05 |
| Formalin solution, 37% | 0.01 |
| Deionized water | 93.34 |
| | 100 |

We claim:

1. A composition consisting essentially of water and an amount of a thickener polymer selected from polymers of Groups A, B and C defined below effective to thicken the water:

Group A:

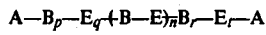

where each of p, q, r and t independently is zero or 1, at least one of q and r is 1,
t is zero when r is zero, and n is at least 1; provided that,
when q is 1, then
  (a) each of p, r and t is zero; or
  (b) p is zero and each of r and t is 1; or
  (c) t is zero and each of r and p is 1; and when q is zero, then r is 1 and each of p and t is zero;

Group B:

where L is X, Y or —O—, Q is —CH$_2$C, D is —CH$_2$O—, m is 2-4, s is zero to 2, the sum of m and s is 2-4, w is 1-3, and each of u, v and z independently is zero or 1;

and where X is a tri- or tetravalent hydrophobic hydrocarbon radical containing at least 3 carbon atoms; and Y is a trivalent hydrophobic radical selected from

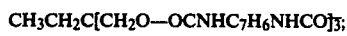

provided that,
  (a) when L is X, then u and w are each 1, v and z are each zero, m is at least 2, and the sum of m and s if 4;
  (b) when L is Y, then u, v and s are each zero, m is 3, w is 2-3, and z is zero or 1; and
  (c) when L is —O—, then v and u are each 1, w is 1-3, m is 2 and each of s and z is zero;

and where, in each of the polymers of Groups A and B: A and R are hydrophobic organic radicals; B is a divalent hydrophobic group of the structure

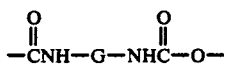

where G is the residue of an organic di- or triisocyanate, said residue having no remaining unreacted isocyanate groups; and E is a divalent, hydrophilic, nonionic polyether group;

Group C:

A composition prepared by reacting (a) a polyfunctional reactant selected from an organic polyol having at least three hydroxyl groups, an organic polyisocyanate having at least three isocyanate groups, and mixtures thereof; (b) a difunctional reactant selected from an organic diol, and organic diisocyanate, and mixtures thereof, said diol being present in the reaction mixture when said polyisocyanate is present and said diisocyanate being present when said polyol is present; (c) a monofunctional hydroxyl or amino compound in an amount sufficient to cap any unreacted isocyanate remaining from the reaction of reactants (a) and (b) and to prevent gelation of the reaction mixture; and optionally (d) an organic monoisocyanate to cap hydroxyl groups remaining from the reaction of reactants (a) and (b); wherein at least one of said polyol and diol contains at least one water soluble polyether segment of at least 1500 molecular weight, and wherein the sum of the carbon atoms in said isocyanate-containing reactants, said hydroxyl compound and said amino compound is at least 20 and the average molecular weight of the components of the composition is about 10,000-200,000.

2. A composition as in claim 1 also containing a coloring composition.

3. A composition as in claim 2 wherein said coloring composition comprises a pigment printing paste.

4. A composition as in claim 2 wherein said coloring composition comprises an acid dyestuff.

5. A composition as in claim 1 wherein the polymer is a polymer of Group A.

6. A composition as in claim 1 wherein the polymer is a polymer of Group B.

7. A composition as in claim 1 wherein the polymer is a polymer of the composition of Group C.

8. A composition consisting essentially of (a) water, (b) at least one substance selected from a water insoluble polymeric material, a cosmetically active material, a topical pharmaceutical, and a pesticidal or herbicidal toxicant, and (c) an effective amount of a thickener selected from polymers of Groups A, B and C as follows:

Group A:

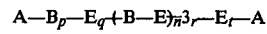

where each of p, q, r and t independently is zero or 1; at least one of q and r is 1, t is zero when r is zero, and n is at least 1;
provided that, when q is 1, then
  (a) each of p, r and t is zero; or
  (b) p is zero and each of r and t is 1; or
  (c) t is zero and each of r and p is 1; and when q is zero, then r is 1 and each of p and t is zero;

Group B:

where L is X, Y or —O—, Q is —CH$_2$C≡, D is —CH$_2$O—, m is 2-4, s is zero to 2, the sum of m and s is 2-4, w is 1-3, and each of u, v and z independently is zero or 1;

and where X is a hydrocarbon radical containing at least 1 carbon atom; and Y is a trivalent radical selected from

provided that, (a) when L is X, then u and w are each 1, v and z are each zero, m is at least 2, and the sum of m and s is 4;
(b) when L is Y, then u, v and s are each zero, m is 3, w is 2–3, and z is zero or 1; and
(c) when L is —O—, then v and u are each 1, w is 1–3, m is 2 and each of s and z is zero;
and where, in each of the polymers of Groups A and B:
A and R are hydrophobic organic radicals;
B is a divalent hydrophobic group of the structure

where G is the residue of an organic di- or triisocyanate, said residue having no remaining unreacted isocyanate groups; and
E is a divalent, hydrophilic, nonionic polyether group; Group C:
A composition prepared by reacting (a) a polyfunctional reactant selected from an organic polyol having at least three hydroxyl groups, an organic polyisocyanate having at least three isocyanate groups, and mixtures thereof; (b) a difunctional reactant selected from an organic diol, an organic diisocyanate, and mixtures thereof, said diol being present in the reaction mixture when said polyisocyanate is present and said diisocyanate being present when said polyol is present; (c) a monofunctional hydroxyl or amino compound in an amount sufficient to cap any unreacted isocyanate remaining from the reaction of reactants (a) and (b) and to prevent gelation of the reaction mixture; and optionally (d) an organic monoisocyanate to cap hydroxyl groups remaining from the reaction of reactants (a) and (b); wherein at least one of said polyol and diol contains at least one water soluble polyether segment of at least 1500 molecular weight, and wherein the sum of the carbon atoms in said isocyanate-containing reactants, said hydroxyl compound and said amino compound is at least 20 and the average molecular weight of the components of the composition is about 10,000–200,000.

9. A composition as in claim 8 wherein said substance (b) is a water insoluble film-forming polymer selected from natural rubber and synthetic addition polymers.

10. A method of thickening a latex composition which comprises incorporating in said composition a polymer selected from polymers of Groups A, B and C as follows:
Group A:

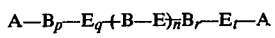

where each of p, q, r, and t independently is zero or 1; at least one of q and r is 1, t is zero when r is zero, and n is at least 1;
provided that,
when q is 1, then
(a) each of p, r and t is zero; or
(b) p is zero and each of r and t is 1; or
(c) t is zero and each of r and p is 1; and when q is zero, then r is 1 and each of p and t is zero;
Group B:

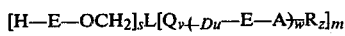

where L is X, Y or —O—, Q is —CH$_2$C≡, D is —CH$_2$O—, m is 2–4, s is zero to 2, the sum of m and s is 2–4, w is 1–3, and each of u, v and z independently is zero or 1;
and where X is a tri- or tetravalent hydrocarbon radical containing at least 1 carbon atom; and Y is a trivalent radical selected from

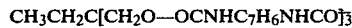

provided that,
(a) when L is X, then u and w are each 1, v and z are each zero, m is at least 2, and the sum of m and s is 4;
(b) when L is Y, then u, v and s are each zero, m is 3, w is 2–3, and z is zero or 1; and
(c) when L is —O—, then v and u are each 1, w is 1–3, m is 2 and each of s and z is zero;
and where, in each of the polymers of Groups A and B:
A and R are hydrophobic organic radicals;
B is a divalent hydrophobic group of the structure

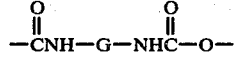

where G is the residue of an organic di- or triisocyanate, said residue having no remaining unreacted isocyanate groups; and
E is a divalent, hydrophilic, nonionic polyether group;
Group C:
A composition prepared by reacting (a) a polyfunctional reactant selected from an organic polyol having at least three hydroxyl groups, an organic polyisocyanate having at least three isocyanate groups, and mixtures thereof; (b) a difunctional reactant selected from an organic diol, an organic diisocyanate, and mixtures thereof, said diol being present in the reaction mixture when said polyisocyanate is present and said diisocyanate being present when said polyol is present; (c) a monofunctional hydroxyl or amino compound in an amount sufficient to cap any unreacted isocyanate remaining from the reaction of reactants (a) and (b) and to prevent gelation of the reaction mixture; and optionally (d) an organic monoisocyanate to cap hydroxyl groups remaining from the reaction of reactants (a) and (b); wherein at least one of said polyol and diol contains at least one water soluble polyether segment of at least 1500 molecular weight, and wherein the sum of the carbon atoms in said isocyanate-containing reactants, said hydroxyl compound and said amino compound is at least 20 and the average molecular weight of the components of the composition is about 10,000–200,000.

11. A method as in claim 10 wherein said polymer is incorporated into said composition in an amount of from about 0.1 to about 10% by weight based upon latex solids in the composition.

12. A method as in claim 10 wherein the polymer is a polymer of Group A.

13. A method as in claim 10 wherein the polymer is a polymer of Group B.

14. A method as in claim 10 wherein the polymer is a polymer of the composition of Group C.

15. A method of thickening an aqueous composition consisting essentially of (a) water and (b) at least one substance selected from a water insoluble polymeric material, a cosmetically active material, a topical pharmaceutical, and a pesticidal or herbicidal toxicant, which method comprises incorporating in said dispersion a polymer selected from polymers of Groups A, B and C as follows:

Group A:

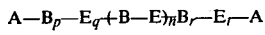

where each of p, q, r and t independently is zero or 1; at least one of q and r is 1, t is zero when r is zero, and n is at least 1;
provided that,
when q is 1, then
(a) each of p, r and t is zero; or
(b) p is zero and each of r and t is 1; or
(c) t is zero and each of r and p is 1; and when q is zero, then r is 1 and each of p and t is zero;

Group B:

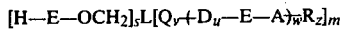

where L is X, Y or —O—, Q is —CH$_2$C≡, D is —CH$_2$O—, m is 2-4, s is zero to 2, the sum of m and s is 2-4, w is 1-3, and each of u, v and z independently is zero or 1;
and where X is a hydrocarbon radical containing at least 1 carbon atom; and Y is a trivalent hydrophobic radical selected from

 and

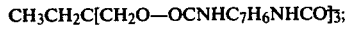

provided that,
(a) when L is X, then u and w are each 1, v and z are each zero, m is at least 2, and the sum of m and s is 4;
(b) when L is Y, then u, v and s are each zero, m is 3, w is 2-3, and z is zero or 1; and
(c) when L is —O—, then v and u are each 1, w is 1-3, m is 2 and each of s and z is zero;
and where, in each of the polymers of Groups A and B:
A and R are hydrophobic organic radicals;
B is a divalent hydrophobic group of the structure

where G is the residue of an organic di- or triisocyanate, said residue having no remaining unreacted isocyanate groups; and
E is a divalent, hydrophilic, nonionic polyether group;

Group C:

A composition prepared by reacting (a) a polyfunctional reactant selected from an organic polyol having at least three hydroxyl groups, an organic polyisocyanate having at least three isocyanate groups, and mixtures thereof; (b) a difunctional reactant selected from an organic diol, an organic diisocyanate, and mixtures thereof, said diol being present in the reaction mixture when said polyisocyanate is present and said diisocyanate being present when said polyol is present; (c) a monofunctional hydroxyl or amino compound in an amount sufficient to cap any unreacted isocyanate remaining from the reaction of reactants (a) and (b) and to prevent gelation of the reaction mixture; and optionally (d) an organic monoisocyanate to cap hydroxyl groups remaining from the reaction of reactants (a) and (b); wherein at least one of said polyol and diol contains at least one water soluble polyether segment of at least 1500 molecular weight, and wherein the sum of the carbon atoms in said isocyanate-containing reactants, said hydroxyl compound and said amino compound is at least 20 and the average molecular weight of the components of the composition is about 10,000–200,000.

16. An aqueous composition consisting essentially of water and an effective amount of a nonionic water soluble or water solubilizable polyurethane thickener composition having at least three hydrophobic groups at least two of which are terminal groups, said hydrophobic groups together containing a total of at least 20 carbon atoms, said hydrophobic groups being linked through hydrophilic polyether groups of at least 1500 molecular weight each, and the molecular weight of said polyurethane being at least 10,000; said polyurethane composition being selected from the following reaction products wherein reactant (a) is at least one water soluble polyether polyol, reactant (b) is at least one water insoluble organic polyisocyanate, reactant (c) is at least one monofunctional hydrophobic organic compound selected from monofunctional active hydrogen containing compounds and organic monoisocyanates, and reactant (d) is at least one polyhydric alcohol or polyhydric alcohol ether;
(1) reaction products of reactant (a) containing at least three hydroxyl groups, and said organic monoisocyanate;
(2) reaction products of reactant (a), reactant (b) containing two isocyanate groups, and said active hydrogen-containing compound;
(3) reaction products of reactant (a), reactant (b) containing at least three isocyanate groups, and said active hydrogen-containing compound;
(4) reaction products of reactant (a), reactant (b) and said monoisocyanate; and
(5) reaction products of reactant (a), reactant (b), said monoisocyanate, and reactant (d).

17. An aqueous composition as in claim 16 also containing a coloring composition.

18. A aqueous composition as in claim 16 wherein said coloring composition comprises a pigment printing paste.

19. An aqueous composition as in claim 16 also containing a substance selected from a water insoluble polymeric material, a topical pharmaceutical, and a pesticidal or herbicidal toxicant.

* * * * *